(12) United States Patent
Chang et al.

(10) Patent No.: US 11,564,983 B1
(45) Date of Patent: Jan. 31, 2023

(54) EFFICIENT EXPRESSION SYSTEM OF SARS-COV-2 RECEPTOR BINDING DOMAIN (RBD), METHODS FOR PURIFICATION AND USE THEREOF

(71) Applicant: Betagen Scientific Limited, Hong Kong (HK)

(72) Inventors: Alan Chang, Severn, MD (US); Fabrizio Maria Anella, Hong Kong (HK); Clement M. Lee, Hong Kong (HK); Bing Lou Wong, Irvine, CA (US)

(73) Assignee: Betagen Scientific Limited, Hong Kong (HK)

( * ) Notice: Subject to any disclaimer, the term of this patent is extended or adjusted under 35 U.S.C. 154(b) by 0 days.

(21) Appl. No.: 17/584,354

(22) Filed: Jan. 25, 2022

Related U.S. Application Data

(60) Provisional application No. 63/235,182, filed on Aug. 20, 2021.

(51) Int. Cl.
*A61K 39/12* (2006.01)
*A61P 31/14* (2006.01)
*C07K 14/005* (2006.01)
*C07K 16/10* (2006.01)
*A61K 39/00* (2006.01)

(52) U.S. Cl.
CPC .............. *A61K 39/12* (2013.01); *A61P 31/14* (2018.01); *C07K 14/005* (2013.01); *C07K 16/10* (2013.01); *A61K 2039/575* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| | | | |
|---|---|---|---|
| 11,179,459 B1 | 11/2021 | Jang et al. | |
| 2010/0240083 A1* | 9/2010 | Sonderegger | C12Q 1/37 530/380 |
| 2020/0339704 A1 | 10/2020 | Bradner et al. | |

FOREIGN PATENT DOCUMENTS

| | | |
|---|---|---|
| AU | 2015271899 A1 | 1/2016 |
| CN | 112359063 A | 2/2021 |
| WO | 03102196 A1 | 12/2003 |
| WO | 2021014385 A1 | 1/2021 |
| WO | 2021074449 A1 | 4/2021 |
| WO | 2021207592 A1 | 10/2021 |
| WO | 2021221486 A1 | 11/2021 |
| WO | 2021229450 A1 | 11/2021 |
| WO | 2021262672 A1 | 12/2021 |

OTHER PUBLICATIONS

Bierig et al., Frontiers in Bioengineering and Biotechnology, Dec. 21,2020, vol. 8., Article 618615, 10 pages. (Year: 2020).*
UniProtKB-P0DTC2 Spike glycoprotein SARS2, Apr. 22, 2020. (Year: 2020).*
Bochkov and Palmenberg, BioTechniques, 2006, 41(3):283-292, printout is pp. 1-10. (Year: 2006).*
Attallah et al., Protein Expression and Purification, 2017, 132:27-33. (Year: 2017).*
Kapust et al., Biochemical and Biophysical Research Communications, 2002, 294:949-955. (Year: 2002).*
Julian Taylor-Parker, addgene Blog, Plasmids 101: Terminators and PolyA signals, available from blog.addgene.org/plasmids-101-terminators-and-polya-signals, Mar. 2016, printout Jul. 7, 2022, 19 pages. (Year: 2016).*
John Lok Man Law, et al. "SARS-COV-2 recombinant Receptor-Binding-Domain (RBD) induces neutralizing antibodies against variant strains of SARS-CoV-2 and SARS-CoV-1.", Vaccine 39(2021), Elsevier Ltd., 5769-5779.
Li, T.T et al., "A synthetic nanobody targeting RBD protects hamsters from SARS-CoV-2 infection.", Nature Communications, No. 12 (2021). https://doi.org/10.1038/s41467-021-24905-z.
Sinegubova MV, et al. (2021), "High-level expression of the monomeric SARS-CoV-2 S protein RBD 320-537 in stably transfected CHO cells by the EEF1A1-based plasmid vector.", PLOS One 16(2): e0242890. https://doi.org/10.1371/journal.pone.0242890.
Jennifer Mehalko, et al., "Improved production of SARS-CoV-2 spike receptor-binding domain (RBD) for serology assays", bioRxiv 18, (2020). doi: https://doi.org/10.1101/2020.11.18.388868.
International Search Report and Written Opinion of corresponding PCT Patent Application No. PCT/CN2022/113637 dated Nov. 17, 2022.

* cited by examiner

*Primary Examiner* — Stacy B Chen
(74) *Attorney, Agent, or Firm* — Idea Intellectual Limited; Margaret A. Burke; Sam T. Yip

(57) ABSTRACT

The present invention relates to the production of the receptor binding domain (RBD) of the Spike glycoprotein 1 of the SARS-CoV-2 in mammalian cell expression systems, and the successive method of purification thereof. A recombinant plasmid containing the coding sequence of said RBD is produced and transfected in said mammalian cells, for example, Expi293. A high level of the protein is secreted in the medium and subsequently purified using the N-terminal tag, that can be removed by a specific protease. The present invention also includes a recombinant expression vector carrying the RBD gene, the successive methods for protein purification, the strategy for establishing a stable cell line producing the RBD, methods of use of the recombinant protein in formulating a pharmaceutical composition, including but not limited to, vaccines for preventing SARS-CoV-2 induced diseases.

14 Claims, 20 Drawing Sheets

Specification includes a Sequence Listing.

Optimized Nucleotide Sequence for Expression Receptor Binding Domain (RBD)

agggtgcagcccaccgagagcatcgtgaggttcccaaatcaccaactgtgccccttcggcgagtgttcaacgccacc
aggttcgccagcgtgtacgcctggaacaggaagaggatcagcaactgcgtggccgactacagcgtgctgtacaacagcgc
cagcttcagcaccttcaagtgctacggcgtgagccctaccaagatcaacgatctgtgttccaacaactacctgcgacgagc
ttcgtgatcagggcgacgaggtgaggcagatcgcccccggcacagagtgcgcgatgctgctaccaactacaagtgcc
cgacgacttcacgcggctgcgtgatcgcctgaacgcaacctgaacagcaacgaaggcaactacaactacctgt
acaggctgttcaggaagagcaacctgaagccctttgagagggacatcagcaccgagatctaccagggggcgcagccccc
tgcaacggcgtggaggttcacatgctactccccgcagctgcccaccgagctcacacgggtgcggttggtacccag
ccctacacagggtggtgctggcttgagctgctgcacgccccagctgcacggtgcggcccaaggaagcaccaacta Amino Acid Sequence Receptor Binding Domain (RBD)

RVQPTESIVRFPNITNLCPFGEVFNATRFASVYAWNRKRISNCVADYSVLYNSASFST
FKCYGVSPTKLNDLCFTNVYADSFVIRGDEVRQIAPGQTGKIADYNYKLPDDFTGCVI
AWNSNNLDSKVGGNYNYLYRLFRKSNLKPFERDISTEIYQAGSTPCNGVEGFNCYFPL
QSYGFQPTNGVGYQPYRVVVLSFELLHAPATVCGPKKSTN

Figure 2

RBD (ExpiCHO)

| Position | Type | sum intensity | Glycosylation efficiency % | Position | Type | sum intensity | Glycosylation efficiency % |
|---|---|---|---|---|---|---|---|
| 6 (T323) | O-Glyco | 9.21E+11 | 85.04 | 54 | O-Glyco | 1.42E+08 | 0.09 |
|  | non | 1.62E+11 |  |  | non | 1.61E+11 |  |
| 8 | O-Glyco | 3.86E+10 | 3.80 | 56 | O-Glyco | 1.38E+09 | 0.86 |
|  | non | 9.77E+11 |  |  | non | 1.59E+11 |  |
| 14 (N331) | N-Glyco | 1.56E+11 | 95.82 | 59 | O-Glyco | 6.17E+07 | 0.04 |
|  | non | 6.81E+09 |  |  | non | 1.61E+11 |  |
| 16 | O-Glyco | 1.87E+09 | 1.15 | 66 | O-Glyco | 2.32E+08 | 0.06 |
|  | non | 1.61E+11 |  |  | non | 3.72E+11 |  |
| 26 (N343) | N-Glyco | 6.19E+11 | 95.74 | 68 | O-Glyco | 4.52E+07 | 0.01 |
|  | non | 2.76E+10 |  |  | non | 3.72E+11 |  |
| 28 | O-Glyco | 2.55E+10 | 3.94 | 76 | O-Glyco | 3.75E+08 | 0.02 |
|  | non | 6.21E+11 |  |  | non | 1.92E+12 |  |
| 32 | O-Glyco | 3.00E+09 | 0.46 | 82 | O-Glyco | 3.86E+09 | 0.20 |
|  | non | 6.55E+11 |  |  | non | 1.91E+12 |  |
| 42 | O-Glyco | 8.23E+08 | 0.50 | 98 | O-Glyco | 1.03E+09 | 0.20 |
|  | non | 1.63E+11 |  |  | non | 5.01E+11 |  |
| 49 | O-Glyco | 2.73E+09 | 1.70 | 113 | O-Glyco | 1.44E+09 | 0.14 |
|  | non | 1.58E+11 |  |  | non | 1.03E+12 |  |

RBD (Expi293)

| Position | Type | sum intensity | Glycosylation efficiency % | Position | Type | sum intensity | Glycosylation efficiency % |
|---|---|---|---|---|---|---|---|
| 6 (T323) | O-Glyco | 5.96E+11 | 6.25 | 49 | O-Glyco | 1.29E+09 | 1.42 |
|  | non | 8.94E+12 |  |  | non | 8.93E+10 |  |
| 8 | O-Glyco | 4.72E+09 | 0.80 | 54 | O-Glyco | 5.07E+08 | 0.56 |
|  | non | 5.82E+11 |  |  | non | 8.99E+10 |  |
| 14 (N331) | N-Glyco | 1.21E+11 | 95.14 | 56 | O-Glyco | 1.03E+09 | 1.14 |
|  | non | 6.15E+09 |  |  | non | 8.93E+10 |  |
| 16 | O-Glyco | 2.65E+09 | 2.09 | 58 | O-Glyco | 3.82E+06 | 0.00 |
|  | non | 1.24E+11 |  |  | non | 9.04E+10 |  |
| 26 (N343) | N-Glyco | 6.21E+11 | 96.63 | 66 | O-Glyco | 1.03E+08 | 0.06 |
|  | non | 2.17E+10 |  |  | non | 1.83E+11 |  |
| 28 | O-Glyco | 2.03E+10 | 3.15 | 76 | O-Glyco | 8.74E+07 | 0.01 |
|  | non | 6.22E+11 |  |  | non | 1.53E+12 |  |
| 32 | O-Glyco | 9.70E+09 | 1.28 | 82 | O-Glyco | 3.78E+09 | 0.25 |
|  | non | 7.45E+11 |  |  | non | 1.53E+12 |  |
| 42 | O-Glyco | 7.45E+08 | 0.80 | 98 | O-Glyco | 3.29E+08 | 0.10 |
|  | non | 9.21E+10 |  |  | non | 3.25E+11 |  |

FIG.6

ELISPOT – Th1 Response (IFNg)

| Sample N° | GROUP ID | Cell number started | Negative control | | | | SARS-CoV-2 RBD Peptide Pool | | | | Positive control | | | |
|---|---|---|---|---|---|---|---|---|---|---|---|---|---|---|
| | | | R 1 IFNg expression | R 2 IFNg expression | R 3 IFNg expression | Mean IFNg expression | R 1 IFNg expression | R 2 IFNg expression | R 3 IFNg expression | Mean IFNg expression | R 1 IFNg expression | R 2 IFNg expression | R 3 IFNg expression | Mean IFNg expression |
| 1 | 1 | 300000 | 0 | 0 | 0 | 0.00 | 0 | 1 | 0 | 0.33 | TNTC | TNTC | TNTC | TNTC |
| 2 | 1 | 300000 | 0 | 0 | 0 | 0.00 | 1 | 1 | 2 | 1.33 | TNTC | TNTC | TNTC | TNTC |
| 3 | 1 | 300000 | 0 | 0 | 0 | 0.00 | 3 | 3 | 0 | 2.00 | TNTC | TNTC | TNTC | TNTC |
| 4 | 1 | 300000 | 0 | 0 | 0 | 0.00 | 4 | 1 | 1 | 2.00 | TNTC | TNTC | TNTC | TNTC |
| 5 | 2 | 300000 | 1 | 1 | 0 | 0.67 | 1 | 4 | 1 | 2.00 | TNTC | TNTC | TNTC | TNTC |
| 6 | 2 | 300000 | 0 | 0 | 0 | 0.00 | 0 | 0 | 1 | 0.33 | TNTC | TNTC | TNTC | TNTC |
| 7 | 2 | 300000 | 0 | 0 | 1 | 0.33 | 2 | 1 | 0 | 1.00 | TNTC | TNTC | TNTC | TNTC |
| 8 | 2 | 300000 | 0 | 0 | 0 | 0.00 | 2 | 2 | 2 | 2.00 | TNTC | TNTC | TNTC | TNTC |
| 9 | 3 | 300000 | 0 | 0 | 0 | 0.00 | 2 | 4 | 2 | 2.67 | TNTC | TNTC | TNTC | TNTC |
| 10 | 3 | 300000 | 0 | 0 | 0 | 0.00 | 3 | 0 | 1 | 1.33 | TNTC | TNTC | TNTC | TNTC |
| 11 | 3 | 300000 | 0 | 0 | 0 | 0.00 | 0 | 3 | 1 | 1.33 | TNTC | TNTC | TNTC | TNTC |
| 12 | 3 | 300000 | 0 | 0 | 0 | 0.00 | 1 | 0 | 1 | 0.67 | TNTC | TNTC | TNTC | TNTC |
| 13 | 4 | 300000 | 0 | 0 | 0 | 0.00 | 3 | 0 | 0 | 1.00 | TNTC | TNTC | TNTC | TNTC |
| 14 | 4 | 300000 | 1 | 0 | 0 | 0.33 | 2 | 4 | 2 | 2.67 | TNTC | TNTC | TNTC | TNTC |
| 15 | 4 | 300000 | 0 | 0 | 0 | 0.00 | 3 | 1 | 0 | 1.33 | TNTC | TNTC | TNTC | TNTC |
| 16 | 4 | 300000 | 0 | 0 | 0 | 0.00 | 0 | 1 | 2 | 1.00 | TNTC | TNTC | TNTC | TNTC |
| 17 | 5 | 300000 | 0 | 0 | 0 | 0.00 | 0 | 0 | 0 | 0.00 | TNTC | TNTC | TNTC | TNTC |
| 18 | 5 | 300000 | 0 | 0 | 0 | 0.00 | 0 | 0 | 1 | 0.33 | TNTC | TNTC | TNTC | TNTC |
| 19 | 6 | 300000 | 1 | 1 | 0 | 0.67 | 1 | 0 | 0 | 0.33 | TNTC | TNTC | TNTC | TNTC |
| 20 | 6 | 300000 | 0 | 0 | 0 | 0.00 | 0 | 2 | 0 | 0.67 | TNTC | TNTC | TNTC | TNTC |
| 21 | 7 | 300000 | 0 | 0 | 0 | 0.00 | 0 | 0 | 0 | 0.00 | TNTC | TNTC | TNTC | TNTC |
| 22 | 7 | 300000 | 0 | 0 | 0 | 0.00 | 0 | 1 | 0 | 0.33 | TNTC | TNTC | TNTC | TNTC |

Figure 18

ELISPOT – Th2 Response (IL-4)

| Sample N° | GROUP ID | Cell number started | Negative control R1 IL-4 expression | R2 IL-4 expression | R3 IL-4 expression | Mean IL-4 expression | SARS-CoV-2 RBD Peptide Pool R1 IL-4 expression | R2 IL-4 expression | R3 IL-4 expression | Mean IL-4 expression | Positive control R1 IL-4 expression | R2 IL-4 expression | R3 IL-4 expression | Mean IL-4 expression |
|---|---|---|---|---|---|---|---|---|---|---|---|---|---|---|
| 1 | 1 | 300000 | 1 | 4 | 4 | 3.00 | 48 | 46 | 42 | 45.33 | TNTC | TNTC | TNTC | TNTC |
| 2 | 1 | 300000 | 15 | 12 | 20 | 15.67 | 159 | 161 | 157 | 159.00 | TNTC | TNTC | TNTC | TNTC |
| 3 | 1 | 300000 | 17 | 28 | 21 | 22.00 | 156 | 147 | 162 | 155.00 | TNTC | TNTC | TNTC | TNTC |
| 4 | 1 | 300000 | 11 | 7 | 17 | 11.67 | 209 | 168 | 153 | 176.67 | TNTC | TNTC | TNTC | TNTC |
| 5 | 2 | 300000 | 10 | 11 | 16 | 12.33 | 97 | 73 | 69 | 79.67 | TNTC | TNTC | TNTC | TNTC |
| 6 | 2 | 300000 | 6 | 14 | 15 | 11.67 | 187 | 190 | 152 | 176.33 | TNTC | TNTC | TNTC | TNTC |
| 7 | 2 | 300000 | 8 | 7 | 12 | 9.00 | 123 | 165 | 130 | 139.33 | TNTC | TNTC | TNTC | TNTC |
| 8 | 2 | 300000 | 3 | 10 | 5 | 6.00 | 120 | 143 | 108 | 123.67 | TNTC | TNTC | TNTC | TNTC |
| 9 | 3 | 300000 | 3 | 6 | 4 | 4.33 | 68 | 56 | 56 | 60.00 | TNTC | TNTC | TNTC | TNTC |
| 10 | 3 | 300000 | 3 | 9 | 10 | 7.33 | 146 | 151 | 130 | 142.33 | TNTC | TNTC | TNTC | TNTC |
| 11 | 3 | 300000 | 4 | 8 | 7 | 6.67 | 82 | 74 | 92 | 82.67 | TNTC | TNTC | TNTC | TNTC |
| 12 | 3 | 300000 | 2 | 9 | 11 | 7.00 | 68 | 59 | 68 | 65.33 | TNTC | TNTC | TNTC | TNTC |
| 13 | 4 | 300000 | 6 | 9 | 9 | 8.00 | 70 | 71 | 73 | 71.33 | TNTC | TNTC | TNTC | TNTC |
| 14 | 4 | 300000 | 0 | 2 | 3 | 1.67 | 65 | 89 | 51 | 68.00 | TNTC | TNTC | TNTC | TNTC |
| 15 | 4 | 300000 | 0 | 8 | 4 | 4.00 | 90 | 79 | 107 | 92.00 | TNTC | TNTC | TNTC | TNTC |
| 16 | 4 | 300000 | 1 | 5 | 8 | 4.67 | 136 | 163 | 124 | 141.00 | TNTC | TNTC | TNTC | TNTC |
| 17 | 5 | 300000 | 0 | 3 | 4 | 2.33 | 5 | 4 | 2 | 3.67 | TNTC | TNTC | TNTC | TNTC |
| 18 | 5 | 300000 | 2 | 2 | 1 | 1.67 | 1 | 5 | 4 | 3.33 | TNTC | TNTC | TNTC | TNTC |
| 19 | 6 | 300000 | 1 | 3 | 5 | 3.00 | 2 | 2 | 4 | 2.67 | TNTC | TNTC | TNTC | TNTC |
| 20 | 6 | 300000 | 2 | 3 | 7 | 3.00 | 5 | 3 | 4 | 4.00 | TNTC | TNTC | TNTC | TNTC |
| 21 | 7 | 300000 | 3 | 3 | 5 | 3.33 | 4 | 6 | 4 | 4.67 | TNTC | TNTC | TNTC | TNTC |
| 22 | 7 | 300000 | 0 | 2 | 0 | 0.67 | 3 | 1 | 2 | 2.00 | TNTC | TNTC | TNTC | TNTC |

Figure 19

EFFICIENT EXPRESSION SYSTEM OF SARS-COV-2 RECEPTOR BINDING DOMAIN (RBD), METHODS FOR PURIFICATION AND USE THEREOF

CROSS-REFERENCE TO RELATED APPLICATIONS

The present application claims priority from U.S. provisional patent application Ser. No. 63/235,182 filed Aug. 20, 2021, and the disclosure of which is incorporated herein by reference in its entirety.

FIELD OF THE INVENTION

The present invention relates to the field of biotechnology, in particular to a SARS-CoV-2-RBD eukaryotic protein expression vector, a preparation method and application thereof, in particular, a mammalian expression system for expressing at least a portion of a receptor binding domain (RBD) of SARS-CoV-2. The present invention also relates to methods of using purified RBD from the system in a pharmaceutical formulation, such as a Covid-19 vaccine.

BACKGROUND OF THE INVENTION

Several outbreaks in the past two decades have been caused by coronaviruses such as the two caused by SARS-CoV-1 and MERS-CoV in 2003 and 2012, respectively. An outbreak infection of a novel coronavirus emerged in late 2019 and has been rapidly spreading across countries causing a significant threat to international health and the economy. The disease caused by this coronavirus was named as COVID-19.

Since then, the world has experienced a grave situation of global public health emergency due to the viral pandemic of severe febrile pneumonia-like respiratory syndrome caused by the novel SARS-CoV-2. This name was chosen by WHO because the virus is genetically related to the coronavirus responsible for the SARS outbreak of 2003. However, the most important structural protein, the spike glycoprotein (S), is slightly different in these viruses. The S protein belongs to class I fusion protein that mediates attachment of the virus to angiotensin converting enzyme 2 (ACE2) of the host cell receptor. Since the spike glycoprotein of SARS-CoV-2 mediates entry of virus into the host cell, it is one of the most important antigenic determinants, making it a potential candidate for a vaccine.

SARS-CoV-2 Spike Protein (S Protein) is a glycoprotein that mediates membrane fusion and viral entry. The S protein is homotrimeric, with each ~180-kDa monomer consisting of two subunits, S1 and S2. In SARS-CoV-2, as with most coronaviruses, proteolytic cleavage of the S protein into two distinct peptides, 51 and S2 subunits, is required for activation. The 51 subunit is focused on attachment of the protein to the host receptor while the S2 subunit is involved with cell fusion. Based on structural biology studies, the receptor binding domain (RBD), located in the C-terminal region of S1, can be oriented either in the up/standing or down/lying state. The standing state is associated with higher pathogenicity and both SARS-CoV-1 and MERS can access this state due to the flexibility in their respective RBDs. A similar two-state structure and flexibility is found in the SARS-CoV-2 RBD. Based on amino acid (aa) sequence homology, the SARS-CoV-2 S1 subunit RBD has a 73% identity with the RBD of the SARS-CoV-1 S1 RBD, but only 22% homology with the MERS 51 RBD. The low aa sequence homology is consistent with the finding that SARS and MERS bind different cellular receptors. The S protein of the SARS-CoV-2 virus, like the SARS-CoV-1 counterpart, binds Angiotensin-Converting Enzyme 2 (ACE2), but with much higher affinity and faster binding kinetics. Before binding to the ACE2 receptor, structural analysis of the 51 trimer shows that only one of the three RBD domains in the trimeric structure is in the "up" conformation. This is an unstable and transient state that passes between trimeric subunits but is nevertheless an exposed state to be targeted for neutralizing antibody therapy. Polyclonal antibodies to the RBD of the SARS-CoV-2 protein have been shown to inhibit interaction with the ACE2 receptor, confirming RBD as an attractive target for vaccinations or antiviral therapy. There is also promising work showing that the RBD may be used to detect the presence of neutralizing antibodies present in a patient's bloodstream, consistent with developed immunity after exposure to the SARS-CoV-2 virus.

Recently, the receptor binding domain (RBD) has been identified as a key viral element allowing virus docking to target cells. It is critical to define the RBD in SARS-CoV-2 in order to deeply understand the infective mechanism of the virus. Moreover, RBD of S protein is also a good target for antiviral therapies because blockading the binding of S protein to cellular receptor can prevent virus entry.

Therefore, there is a need to guarantee a high yield of expression for RBD through careful design of an appropriate vector, selecting an appropriate cell line for expression of the protein and related the purification methods, and provide a stable production of RBD at higher yield in a shorter period of time compared to the existing inventions. This invention addresses this need along with the use of expressed RBD in various covid therapeutics.

SUMMARY OF THE INVENTION

Accordingly, the present invention provides an expression vector with high expression level of a secreted SARS-COV-2-RBD and a method for purifying SARS-COV-2-RBD. There is also provided a strategy for developing a transfected mammalian cell for the expression of RBD as well as a high yield of highly purified Receptor Binding Domain (RBD) of SARS-COV-2 from mammalian cells. There is further provided a production method, including expression and purification, of said RBD in mammalian cells. Additionally, there is provided a recombinant expression vector including the cDNA of said RBD. Potential use of said RBD in formulating various pharmaceutical compositions, such as a vaccine to prevent or treating a coronavirus infected subject, is also described herein. Moreover, the RBD produced from the present invention can be utilized as an antigen in a vaccine formulation to elicit the neutralization antibody so as to prevent SARS-CoV-2-induced diseases.

In one aspect, the present invention provides a SARS-CoV-2-RBD eukaryotic protein expression vector, a preparation method and application thereof, in particular, an expression vector for use in a mammalian expression system for expressing said SARS-CoV-2-RBD efficiently with high purity, low endotoxicity, high yield, low in cytoplasmic content of the host cell, thereby reducing the chance of adverse effect caused by exogenous materials when said RBD is formulated as a pharmaceutical composition for administering to a subject in need thereof. In a preferred embodiment, the expression vector includes a gene reporter, a signal peptide from Human Serum Albumin (HSA) or human Granulocyte colony-stimulating factor (h-GCSF), an affinity purification tag, a recognition site for a protease and a coding sequence for said RBD.

In another aspect of the present invention, a method is provided for establishing a stable cell line for the expression of high yield of said RBD.

In another aspect of the present invention, methods of using the produced SARS-COV2-RBD are provided in various types of pharmaceutical compositions, including but not limited to, a vaccine for the prevention of SARS-CoV-2 associated diseases and/or symptoms.

Advantageously, the present invention provides 1) less risk of endotoxin contaminations than the RBD produced in E. coli; 2) Express higher protein yield in less time, resulting in less labor and other costs (plasticware and reagents); 3) Beneficial balance between speed, cost and safety of the production compared to other expression systems; 4) The system provides a large amount of proteins with consistent quality and regulatory familiarity; 5) The serum-free medium reduces risk of animal component-associated infections as the has been medium adapted to be animal-origin-free to ensure patient safety. The demand for animal-origin free culture medium has been at the forefront of many biopharmaceutical companies in terms of drug development and production; 6) The ability to maintain constitutive expression and high yield of the protein under animal-origin free conditions is therefore highly desirable; 7) The high synergy between the expression vector and the cell line allows for a high production of RBD protein; and 8) The fact that the RBD is produced in mammalian cell guarantees for the correct folding of the protein for human use; 9) Vaccines produced according to the present invention may be stored at conventional refrigeration temperatures. 10) The vaccine formulation based on this invention can elicit a high titer of neutralizing antibodies effective against the SARS-CoV-2 wild type virus and all its known variants.

BRIEF DESCRIPTION OF THE DRAWINGS

Embodiments of the invention are described in more details hereinafter with reference to the drawings, in which:

FIG. 2 depicts the optimized codon DNA sequence for the expression of RBD in mammalian cells (SEQ ID NO:1) and amino acid sequence of the produced RBD (SEQ ID NO: 2).

FIG. 6 illustrates the results of the glycosylation profile for the RBD-CoV-S polypeptide of SEQ ID NO: 1 purified from ExpiCHO and Expi293 Cells.

FIG. 18 depicts the Th1 response after immunizing the mice with RBD and Alumn.

FIG. 19 depicts the Th2 response after immunizing the mice with RBD and Alumn.

DEFINITIONS

Figure 1:
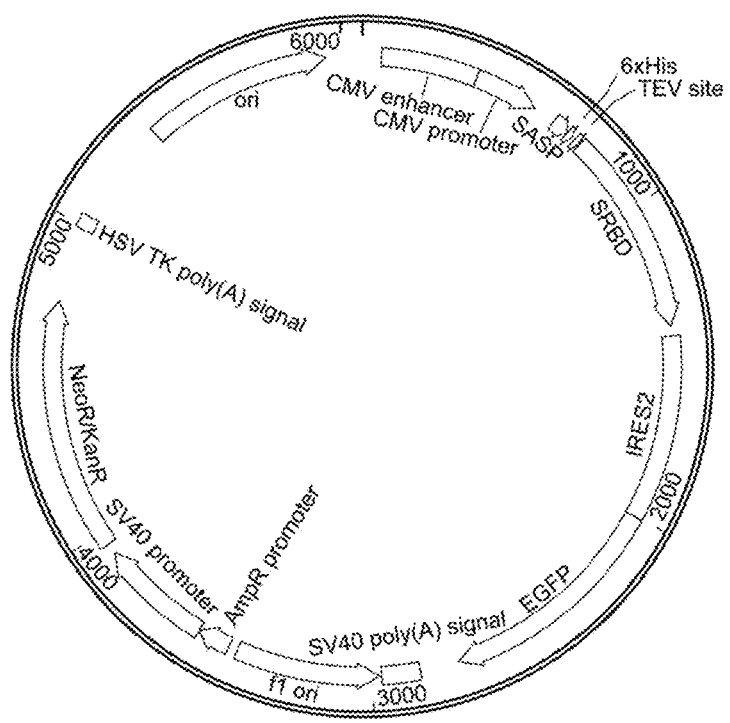
FIG. 1 depicts the schematic map of the vector pIRES2_RBD_eGFP expressing the recombinant polypeptide RBD.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of preparation described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

The term "vector" as used herein refers to a composition having a polynucleotide capable of carrying at least one exogenous nucleic acid fragment, e.g., a plasmid vector, a transposon, a cosmid, or an artificial chromosome such as a human artificial chromosome (HAC), a yeast artificial chromosome (YAC), a bacterial artificial chromosome (BAC), or a PI-derived artificial chromosome (PAC).

The term "expression" as used herein refers to the transcription and/or translation of a particular nucleotide sequence encoding a protein.

The term "promoter" as used herein refers to a DNA sequence recognized by enzymes or proteins (e.g., RNA polymerase and/or associated with binding factors) in a cell required to initiate the transcription of a specific gene (e.g., a SARS CoV-2 polypeptide or fragment thereof).

The term "poly(A) nucleotide sequence" is a sequence which is able to initiate the endonuclease cleavage of mRNA and the additional of a series of adenosines to the 3' end of the cleaved mRNA.

The term "transfected" or "transformed" refers to a process by which exogenous nucleic acid is transferred or introduced into a cell.

The term "affinity tag" as used herein refers to a unique polypeptide that can be attached to N- or C-terminus of the recombinant proteins so as to facilitate protein purification.

DETAILED DESCRIPTION

In the following description, it will be apparent to those skilled in the art that modifications, including additions and/or substitutions may be made without departing from the scope and the spirit of the invention. Specific details may be omitted so as not to obscure the invention; however, the disclosure is written to enable one skilled in the art to practice the teachings herein without undue experimentation.

As shown in FIG. 1, in one aspect the present invention provides an expression vector for producing a recombinant SARS-CoV-2 polypeptide or a fragment thereof. SARS-CoV-2, where the recombinant SARS-CoV-2 polypeptide or fragment thereof is a bicistronic structure. The bicistronic structure is able to reduce the influence of genetic context on target gene expression, leading to improve the reliability and stability of a strong expression vector. The expression vector in the present invention includes at least one polynucleotide sequence encoding at least one signal peptide sequence, at least one affinity tag, at least one protease recognition site sequence, at least one reporter sequence, and a receptor-binding domain (RBD) sequence of SARS-CoV-2 spike glycoprotein, where the RBD corresponding to the residues 319 to 532 of the Spike protein of the SARS-CoV-2 (NCBI Reference Sequence: YP_009724390.1).

In another aspect of the present invention, the expression vector is transfected into a human-derived host cell, such that the human-derived host cell is able to perform complex post-translational modifications and fold the protein correctly. In addition, the recombinant SARS-CoV-2 polypeptide or fragment thereof was produced in a serum-free medium so as to reduce the risk of animal component contamination. Consequently, any therapeutics such as vaccine compositions using the expressed recombinant RBD or RBD fragment is able to induce strong and specific cell-mediated immunity and high neutralizing antibody titers against various strains of SARC-CoV-2 coronavirus.

In one embodiment, the expression vector includes a polynucleotide sequence encoding a RBD sequence of SARS-CoV-2 spike glycoprotein. In one embodiment, the RBD sequence of SARS-CoV-2 spike glycoprotein has a polynucleotide sequences which is at least 80% (e.g. at least 85%, at least 90%, at least 95%, and at least 100%) identical to SEQ ID NO:1. In one embodiment, the RBD sequence of SARS-CoV-2 spike glycoprotein has an amino acid sequence which is at least 80% (e.g. at least 85%, at least 90%, at least 95%, and at least 100%) identical to SEQ ID NO:2. In one embodiment, a polynucleotide sequence includes the signal peptide sequence, the affinity tag sequence, and the protease recognition site sequence, where the polynucleotide sequence is at least 80% (e.g. at least 85%, at least 90%, at least 95%, and at least 100%) identical to SEQ ID NO: 3. In one embodiment, the polynucleotide sequence including the signal peptide sequence, the affinity tag sequence, and the protease recognition site sequence is operatively linked to the polynucleotide sequence including the RBD sequence of SARS-CoV-2 spike glycoprotein.

```
                                             SEQ ID NO: 1
AGGGTGCAGCCCACCGAGAGCATCGTGAGGTTCCCCAACATCACCAAC

CTGTGCCCCTTCGGCGAGGTGTTCAACGCCACCAGGTTCGCCAGCGTGT

ACGCCTGGAACAGGAAGAGGATCAGCAACTGCGTGGCCGACTACAGC

GTGCTGTACAACAGCGCCAGCTTCAGCACCTTCAAGTGCTACGGCGTG

AGCCCCACCAAGCTGAACGACCTGTGCTTCACCAACGTGTACGCCGAC

AGCTTCGTGATCAGGGGCGACGAGGTGAGGCAGATCGCCCCCGGCCAG

ACCGGCAAGATCGCCGACTACAACTACAAGCTGCCCGACGACTTCACC

GGCTGCGTGATCGCCTGGAACAGCAACAACCTGGACAGCAAGGTGGGC

GGCAACTACAACTACCTGTACAGGCTGTTCAGGAAGAGCAACCTGAAG

CCCTTCGAGAGGGACATCAGCACCGAGATCTACCAGGCCGGCAGCACC

CCCTGCAACGGCGTGGAGGGCTTCAACTGCTACTTCCCCCTGCAGAGCT

ACGGCTTCCAGCCCACCAACGGCGTGGGCTACCAGCCCTACAGGGTGG

TGGTGCTGAGCTTCGAGCTGCTGCACGCCCCCGCCACCGTGTGCGGCCC

CAAGAAGAGCACCAACTA the sequence is as follow:

SEQ ID NO: 2
RVQPTESIVRFPNITNLCPFGEVFNATRFASVYAWNRKRISNCVADYS

VLYNSASFSTFKCYGVSPTKLNDLCFTNVYADSFVIRGDEVRQIAPGQ

TGKIADYNYKLPDDFTGCVIAWNSNNLDSKVGGNYNYLYRLFRKSNLK

PFERDISTEIYQAGSTPCNGVEGFNCYFPLQSYGFQPTNGVGYQPYRVV

VLSFELLHAPATVCGPKKSTN the sequence is as follow:

SEQ ID NO: 3
GAATTCGCCACCATGAAGTGGGTGACCTTCATCAGCCTGCTGTTCCTGT

TCAGCAGCGCCTACAGCCACCACCACCACCACCACAGCAGCGGCGGCG

AGAACCTGTACTTCCAGGGCAGGGTGCAGCCCACCGAGAGCATCGTGA

GGTTCCCCAACATCACCAACCTGTGCCCCTTCGGCGAGGTGTTCAACGC

CACCAGGTTCGCCAGCGTGTACGCCTGGAACAGGAAGAGGATCAGCAA

CTGCGTGGCCGACTACAGCGTGCTGTACAACAGCGCCAGCTTCAGCAC

CTTCAAGTGCTACGGCGTGAGCCCCACCAAGCTGAACGACCTGTGCTTC

ACCAACGTGTACGCCGACAGCTTCGTGATCAGGGGCGACGAGGTGAGG

CAGATCGCCCCCGGCCAGACCGGCAAGATCGCCGACTACAACTACAAG

CTGCCCGACGACTTCACCGGCTGCGTGATCGCCTGGAACAGCAACAAC

CTGGACAGCAAGGTGGGCGGCAACTACAACTACCTGTACAGGCTGTTC

AGGAAGAGCAACCTGAAGCCCTTCGAGAGGGACATCAGCACCGAGAT

CTACCAGGCCGGCAGCACCCCCTGCAACGGCGTGGAGGGCTTCAACTG

-continued

CTACTTCCCCCTGCAGAGCTACGGCTTCCAGCCCACCAACGGCGTGGGC

TACCAGCCCTACAGGGTGGTGGTGCTGAGCTTCGAGCTGCTGCACGCC

CCCGCCACCGTGTGCGGCCCCAAGAAGAGCACCAACTAATGCAGTCGA

C
```

Figure 16:
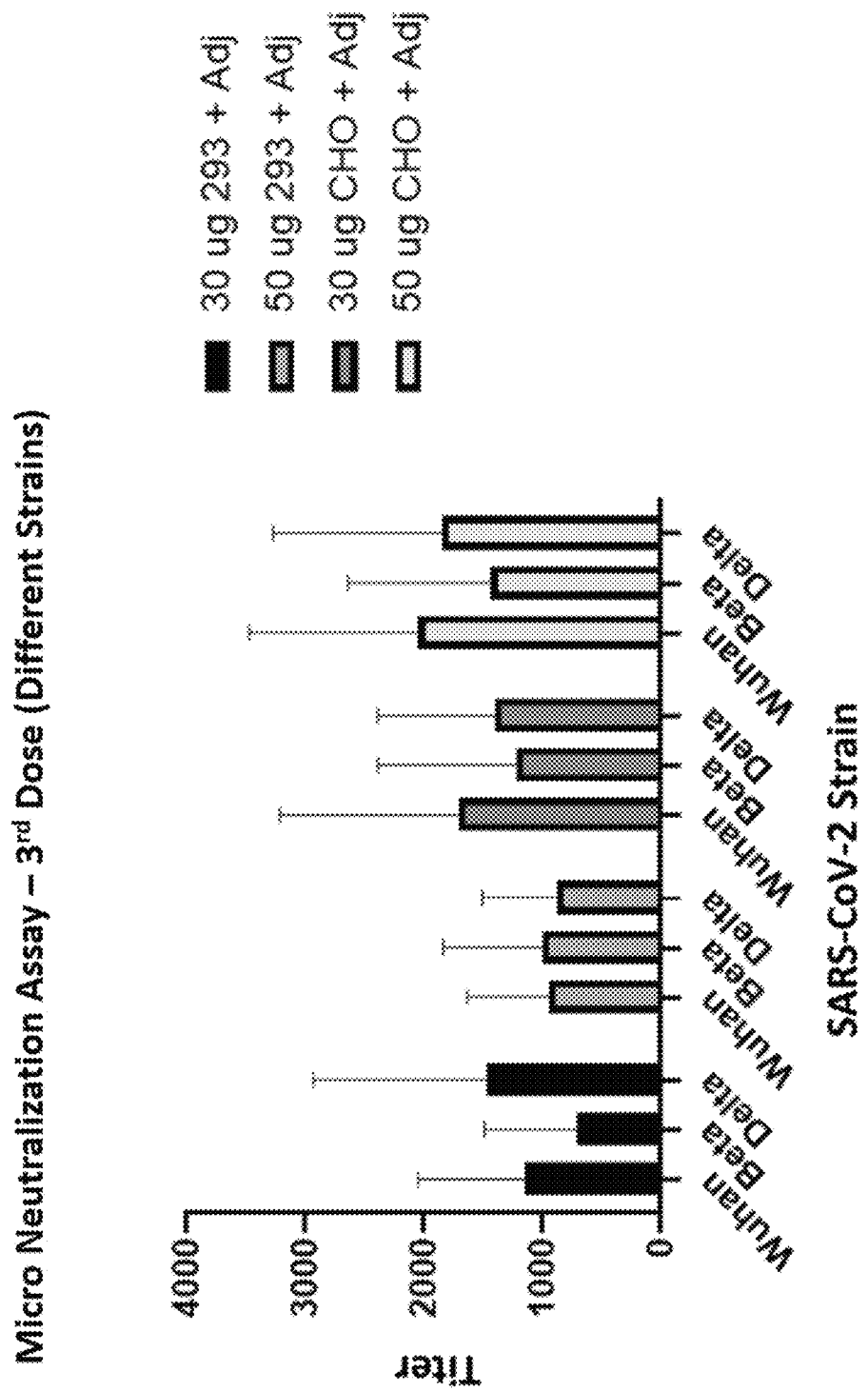
FIG. 16 illustrates the comparison of the titers of the neutralizing antibodies from the mice serum after 14 days of the $3^{rd}$ immunization for the strain wild type (Wuhan-1), B.1.351 (Beta) and B.1.617.2 (Delta).
Figure 17:
FIG. 17 illustrates the illustrates the titers of the neutralizing antibodies against coronavirus Omicron strain (B.1.1.529) from the mice serum after 14 days of the $3^{rd}$ immunization, obtained by a Micro Neutralization Assay with live virus.

Advantageously, as will be discussed in further detail in the examples below, the use of the selected portion of the RBD can induce an immune response with a maximized amount of specific neutralize antibodies compared to an antigen designed on the whole Spike protein of SARS-CoV-2. Furthermore, this choice will decrease the challenges from the emergence of new variants, as a vaccine made from the selected portion of the RBD will not be affected by mutation in area outside of the RBD region of the spike protein. This is proof by the results in FIG. 16 and FIG. 17, in which is shown as antibodies elicited by this vaccine are conserving neutralization activity against variants of interest in current circulation.

In one embodiment, the expression vector includes, for example, but not limited to, cosmids, plasmids (e.g., naked or contained in liposomes), which is able to incorporate the recombinant polynucleotide. In one embodiment, the expression vector is a plasmid and the total length of the expression vector is up to approximately 2 kb, up to approximately 4 kb, up to approximately 6 kb, up to approximately 8 kb, up to approximately 10 kb, up to approximately 12 kb, up to approximately 14 kb, or up to approximately 16 kb. In one embodiment, the expression vector is a plasmid and have a total length in a range approximately from 1 kb to 2 kb, approximately from 1 kb to 4 kb, approximately from 1 kb to 6 kb, approximately from 1 kb to 8 kb, approximately from 1 kb to 10 kb, approximately from 1 kb to 12 kb, approximately from 1 kb to 14 kb, approximately from 1 kb to 16 kb.

To initiate the transcription of the specific gene in the expression vector, the expression vector includes promoter sequence to bind to specific or associated proteins, enzymes, factors, or combinations thereof. In one embodiment, the promoter of the expression vector in the present invention includes for example, but not limited to human cytomegalovirus (CMV), human ubiquitin C (UBC), mouse phosphogly cerate kinase 1, polyoma adenovirus, simian virus 40 (SV40), β-globin, β-actin, α-fetoprotein, δ-globin, β-interferon, γ-glutamyl transferase, ampR promoter or any other known promoters in the art. In one embodiment, the promoter type of the expression vector in the present invention includes for example, but not limited to a constitutive promoter, an inducible promoter, a chimeric promoter, an engineered promoter, or any other type of promoters known in the art. In one embodiment, the promoters of the expression vector comprise SV40 promoter, ampR promoter, CMV promoter or combination thereof.

To further increase the transcriptional level of a specific gene encoding the protein of interest (e.g., RBD sequence of SARS-CoV-2 spike glycoprotein), the expression vector in the present invention further includes an enhancer, where the enhancer includes for example but not limited to a CMV enhancer, a SV40 enhancer or a combination thereof.

The expression vector in the present invention further includes nucleotide signal sequence poly(A) so as to direct proper processing of the 3' end of the transcriptional mRNA or the bicistronic mRNA. In one embodiment, the poly(A) sequence is derived from for example but not limited to the Herpes simplex virus thymidine kinase gene (HSV TK), the group of SV40 poly(A) sites, such as the SV40 late and early poly(A) site, bovine growth hormone (bgh), polyoma virus, or combination thereof. In one embodiment, the poly(A) sequence contains a hexanucleotide sequence for example but not limited to

AATAAA, AAGAAA, AAAAAA, AATGAA, AATCAA, GATAAA, ACTAAA, AATATA.

In order to synthesize more than one polypeptide from a single gene transcript and preserve the folding structure of the polypeptide correctly, the expression vector in the present invention include a polynucleotide internal ribosome entry site (IRES) sequence so as to form a bicistronic structure. In one embodiment, the IRES sequence is operatively linked the RBD sequence of SARS-CoV-2 spike glycoprotein and the reporter sequence. The reporter sequence in the expression vector is able to express detectable signals by means of including but not limited to enzymatic, radiographic, colorimetric, fluorescence, or other spectrographic assays. In one embodiment, the reporter sequence includes a polynucleotide sequence encoding for example but not limited to a β-galactosidase (LacZ), an alkaline phosphatase, a thymidine kinase, an enhanced green fluorescent protein (eGFP), an enhanced red fluorescent protein, an mCherry fluorescent protein, an enhanced yellow fluorescent protein (eYFP), an enhanced red fluorescent protein (eRFP), a chloramphenicol acetyltransferase (CAT), a luciferase, or combination thereof.

The expression vector in the present invention is transfected into host cells by a various methods including but not limited to lipofection, calcium phosphate transfection, transfection using highly branched organic compounds, transfection using cationic, lipid-based transfection, optical transfection, particle-based transfection, or liposome-based transfection. In order to obtain suitable folding proteins having a correct post translational modification profile, in one embodiment, the host cells are human-derived host cells. Skilled practitioners will appreciate that any of the expression vectors described herein can be transfected into a human-derived host cell by, for example, cationic, lipid-based transfection, and can be stably integrated into an endogenous gene locus. In some embodiments, the human-derived host cell is a human embryonic kidney cell.

The polypeptide or recombinant protein encoded from the expression vector in the present invention may further include a signal peptide at the N-terminus, which is a shot peptide having a length of 5 to 50 amino acid residues and the signal peptide is able to direct the expressed proteins or polypeptides to the secretory pathway in the host cell. In some embodiments, the signal peptide is selected from but not limited to murine phosphatase signal peptide sequence, honeybee melittin signal peptide sequence, human albumin signal peptide sequence, human granulocyte colony-stimulating factor or combination thereof.

The polypeptide or recombinant protein encoded from the expression vector in the present invention may also include at least one affinity tag for further protein purification. In some embodiments, the affinity tag includes for example chitin binding protein, maltose binding protein, poly histidine tag, protein A, glutathione S transferase, Glu-Glu affinity tag, substance P, streptavidin binding peptide, zinc fingers, fluorinated polymers, other antigenic epitope or binding domain. In one embodiment, the poly histidine tag having at least six or more consecutive histidine residues is at N-terminus of the recombinant protein.

The polypeptide or recombinant proteins in the present invention may be isolated by using a column, specifically a chromatography column, more specifically an immobilized metal affinity chromatography column (IMAC). The IMAC includes the transition metal ions immobilized on a resin matrix by using a chelating ligand for example but not limited to nitrilotriacetic acid (NTA) or iminodiacetic acid (IDA). The metal ions coupled to the chelating ligands are then attached by the poly histidine tag of the polypeptide or recombinant protein to from a transitional protein complex. In some embodiments, the metal ions include but not limited to copper ($Cu^{2+}$), nickel ($Ni^{2+}$), cobalt ($Co^{2+}$), or zinc ($Zn^{2+}$) ions. In order to remove the impurities and increase the final purity of the recombinant protein, the protein complexes are washed by an imidazole-containing wash buffer. In some embodiments, the imidazole concentration of the wash buffer is approximately from 20 mM to 100 mM, approximately from 20 mM to 80 mM, approximately from 20 mM to 60 mM. To elute the protein complex from the resin matrix in the column, higher imidazole-containing elution buffer have been applied such that the higher concentration of imidazole would compete against the affinity between the poly histidine tag and the metal ion, then elute the polypeptide or recombinant protein from the resin matrix. In some embodiments, the imidazole concentration in the elution buffer is at least 150 mM (e.g., at least 160 mM, at least 170 mM, at least 180 mM, at least 190 mM, and at least 200 mM).

The expression vector in the present invention may further include at least one protease recognition site sequence such that the protease is able to bind to the sequence and remove the affinity tag from the polypeptide or recombinant protein. In some embodiments, the protease is a cysteine proteinase selected from tobacco etch virus (TEV) protease or human rhinovirus (HRV) 3C protease. In one embodiment, the protease recognition site sequence is located between the affinity tag and the RBD sequence of SARS-CoV-2 spike glycoprotein.

The present invention further provides vaccine compositions for preventing or treating SARS-CoV-2 infection, which include products any of the expression vectors described herein. In some embodiments, the vaccine compositions include a pharmaceutically acceptable carrier or excipient. The pharmaceutically acceptable carrier or excipient is selected from for example but not limited to lactose, dextrose, sucrose, mannitol, starch, acacia gum, alginate, gelatin, calcium silicate, microcrystalline cellulose, polyvinylpyrrolidone, water, syrup, methyl cellulose, methylhydroxybenzoate, propylhydroxybenzoate, mineral oil, and combination thereof. The vaccine compositions may include an immunological adjuvant to enhance the immune response effect, and may further include the polypeptides selected from spike protein (S), nucleocapsid (N) protein of SARS-CoV-2, matrix protein (M) of SARS-CoV-2, envelope (E) protein of SARS-CoV-2, or a combination thereof with or without the immunological adjuvant. The adjuvant is selected from for example but not limited to AS03, CpG, squalene (MF59), liposome, TLR agonist, monophosphoryl lipid A (MPL), magnesium hydroxide, titanium dioxide, calcium carbonate, barium oxide, calcium sulfate, calcium pyrophosphate, magnesium carbonate, magnesium oxide, aluminum hydroxide, and hydrated aluminum potassium sulfate (Alum), or a combination thereof.

Also provided herein are methods of inducing immunity to a coronavirus infection in a subject that includes administering to the subject a therapeutically effective amount of any of the products of the expression vectors described herein, for example, as in a as a vaccine composition. In some embodiments, the immunity includes cellular immunity, humoral immunity, or combination thereof. Also provided herein are methods of increasing the titer of neutralizing antibodies in a subject that specifically bind to a SARS-CoV-2 polypeptide or a fragment thereof that includes administering to the subject a therapeutically effective amount of any of the products of the expression vectors described herein. Also provided herein are methods of preventing a coronavirus infection or decreasing the severity of disease related to a coronavirus infection in a subject that includes administering to the subject a therapeutically effective amount of any of the products of the expression vectors described herein contained in any of the vaccine compositions described herein. In some embodiments, the coronavirus is for example but not limited to Wuhan strain/alpha strain beta strain, delta strain, omicron strain or combinations thereof.

EXAMPLES

Example 1: Design and Synthesis of SARS-CoV-2-RBD Gene Sequence Optimized by Codon In order to select and optimize the codons for the expression of the protein in the mammalian cells, an online Codon Optimization Tool, ExpOptimizer developed by NovoPro, is utilized for analyzing the gene sequence of RBD of SARS-CoV-2. The result sequence is shown as SEQ ID NO: 1, and the corresponding artificially synthesizing amino acid sequence is shown in SEQ ID NO: 2, namely a SARS-CoV-2-RBD protein RBD gene sequence optimized by codon (FIG. 2). Additional sequences such as human serum albumin signal peptide, a six histidine tag and the cleavage site for the tobacco etch virus protease have been inserted ahead of the start codon (ATG) upstream of the protein sequence as shown in SEQ ID NO: 3.

The aforementioned sequences were synthesized by Gene Universal., Ltd, and inserted into the vector pIRES2_eGFP by digesting with EcoRI enzyme and SalI enzyme to construct the recombinant plasmid pIRES2_RBD_eGFP. The construct with synthesized sequence is then confirmed by sequencing and enzyme restriction profiles.

Example 2: Plasmid Amplification in *E. coli*

In order to harvest sufficient number of plasmids, 200 pg of the pIRES2_RBD_eGFP plasmid from the example 1 was transformed in DH5a *E. Coli* competent cell by following steps: 2 µl of the plasmid solution in a concentration of 100 µg/µl was added to 50 µl of cell suspension and incubated in ice for 30 minutes. In order to induce the formation of pores to take in the plasmids, the competent cells were heat-shock at 42° C. for 45 seconds, followed by incubation in ice for 2 minutes. Then 1 ml of LB was added to the suspension and incubated at 37° C. for 1 hour under gentle shaking (200 rpm). Then the competent cells with plasmids were plated on LB agar plate containing 50 µg/ml kanamycin and incubated overnight at 37° C. for antibiotic selection. Next day, a single colony was collected and used to inoculate in 1 L LB medium containing 50 µg/ml kanamycin antibiotics. Then the culture was grown at 37° C. for approximately 1 day. The amplified plasmids were harvested by Maxiprep using the PureLink HiPure Plasmid DNA purification kit (Invitrogen). The following buffers or steps were prepared before the purification: Resuspension Buffer (R3) added with RNase A and Lysis Buffer (L7) warmed in a 37° C. water bath. Then more steps were performed as follows: 30 mL Equilibrium Buffer (EQ1) was applied to the HiPure Maxi Column and allowed to drain by gravity flow. The cells were collected by centrifuging at 4000×G for 10 minutes and all medium was removed. The cell pellets were resuspended with 10 mL R3 homogenously. Then, 10 mL L7 was added and mixed gently by inverting the tube 5 times without vortex followed by incubating at room temperature for 5 minutes. 10 mL Precipitation Buffer (N3) was added into the tube and mixed gently by inverting without vortex until the mixture was homogenous. The lysate was centrifuged at 12000×G for 20 minutes at 4° C. The supernatant was loaded onto the equilibrated column and allowed to drain by gravity flow. 60 mL Wash Buffer (W8) was added to the column and allowed to drain by gravity flow and the washing step was performed twice. To collect the eluted plasmid DNA, a 50 mL centrifuge tube was placed under the column followed by adding 15 mL Elution Buffer (E4) to the column and draining by gravity flow. The eluted plasmid DNA was purified with 10.5 mL isopropanol. The tube was centrifuged at 12000×G for 30 minutes at 4° C. and the supernatant was removed. The remaining DNA pellet was washed in 5 mL 70% ethanol. The tube was centrifuged at 12000×G for 5 minutes at 4° C. The supernatant was removed. Finally, the plasmid DNA pellet was allowed to air-dry for 10 minutes, then resuspended in 200 µl water, and stored at −20° C.

Example 3: Transient Expression of RBD Protein in Expi293 and Purification

In order to investigate the protein expression efficiency, the purified plasmid from the example 2 was utilized to transiently transfect in Expi293™ cells. The ExpiFectamine™ 293 transfection kit was used to transfect Expi293F™ cultures by following steps: freshly thawed cells were allowed to recover in culture for 3 or more passages before transfection. Expi293F™ cells were expanded to a density of 3-5×10$^6$ viable cells/mL. One day prior to transfection, the culture was split to achieve a final density of 2.5-3×10$^6$ viable cells/mL so as to allow the cells to grow overnight. On the next day, the viable cell density and the cell viability were measured and it is preferred the viable cell density should be approximately 4.5-5.5×10$^6$ viable cells/mL, and the cell viability should be approximately 95%-99% before further proceeding with transfection. Then, the cells were diluted with fresh Expi293™ Expression Medium (prewarmed to 37° C.) to a density of 3×10$^6$ viable cells/mL. It is preferred to have total plasmid DNA of 1.0 µg per mL culture volume for transfection. ExpiFectamine™ 293/Plasmid DNA mixtures should be prepared in advance with following steps: ExpiFectamine™ 293 reagent bottle were inverted 4-5 times to mix well, and the plasmid DNA was diluted with Opti-MEM™ I Reduced Serum Medium by mixing gently. Then, ExpiFectamine™ 293 Reagent was diluted with Opti-MEM™ I Reduced Serum Medium by gently pipetting and allowed to incubate at room temperature for 5 minutes. And the diluted ExpiFectamine™ 293 Reagent was added to the plasmid DNA to obtain the ExpiFectamine™ 293/Plasmid DNA mixture and mixed by gently pipetting followed by incubating at room temperature for 10-20 minutes. The mixture was transferred slowly to the cells, and the cells were then incubated in a 37° C. incubator with humified atmosphere of 8% $CO_2$ in air on an orbital shaker. 18-22 hours after transfection, ExpiFectamine™ 293 Transfection Enhancer 1 and 2 were added to the culture flasks, and the flasks were then placed in the incubator. Then, the medium was collected approximately 5-7 days post-transfection.

Figure 3B:
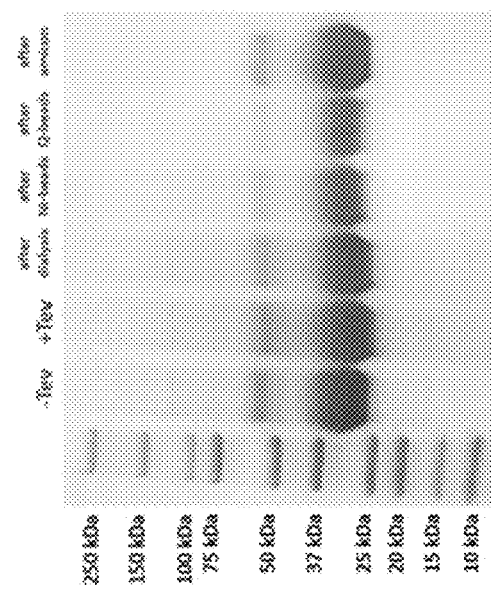
FIG. 3B illustrates the electrophoresis results showing the tag-removal process to remove the 6 histidine at the N-terminus of the expressed recombinant protein (−Tev: RBD before TEV protease digestion; +Tev: RBD with the addition of the TEV protease; after dialysis: RBD sample after TEV digestion overnight and dialysis to remove the imidazole; after Ni-beads: flow-through of the negative affinity purification to isolate the RBD from the TEV protease and the un-cutted RBD; after Q-beads: Flow-through of the anion exchange chromatography to remove the impurity and endotoxin from the RBD sample; after amicon: final RBD sample after concentration with amicon column.
Figure 3A:
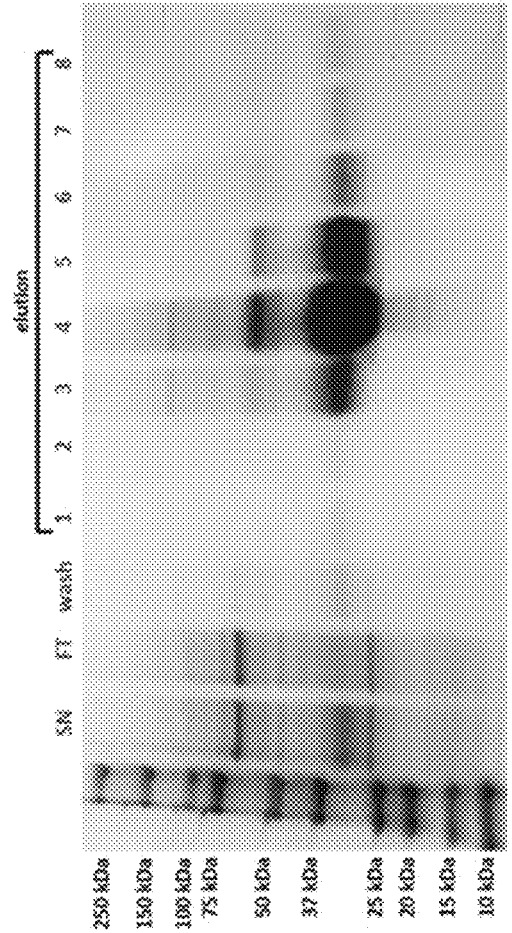
FIG. 3A illustrates the electrophoresis results of the different fractions of the affinity chromatography of the Expi293 medium (SN: supernatant; FT: flow-through; wash: wash buffer with 40 mM imidazole; well 1 to 8: elution fractions with 200 mM imidazole)

In order to remove the impurities, the medium was filtered through 0.22 μm filter membrane and subjected to affinity purification with Ni-NTA beads from Bio-basic (Cat: SA005100) by following steps: 2 ml of the buffer equilibrated Ni-NTA beads were added to the filtered medium and incubated for binding at 4° C. for 2 hours under gentle inversion. The unbound fraction was removed by passing through an Econo-pack column from Bio-rad (Cat: 7321010), with the beads trapped on the bottom of the column. 50 ml of the washing buffer containing either 40 mM imidazole or 80 mM imidazole were used to wash the beads to remove any impurities. Furthermore, the his-tagged RBD was eluted from the beads with buffer containing 200 mM imidazole. As shown in FIG. 3A, samples from each elution step were analyzed by running SDS-PAGE to identify fractions containing RBD protein. Each elution fraction containing his-RBD in 200 mM imidazole buffer (elution-1 to elution-8 in the SDS PAGE in FIG. 3A) was poured together and subjected to a buffer exchange by Amicon Ultra Centrifugal Filter from Millipore (Cat: #UFC901096) to reduce the imidazole concentration below 50 mM. Meanwhile, in order to remove the affinity tag (his-tag) of the his-RBD, the resulting solution was incubated over night with TEV in approximately 1:30 w/w ratio at 4° C. On the next day, the mixture was then incubated with 1 ml of Ni-NTA Beads for 1 hour at 4° C., under gentle mix. The mixture was successively passed through an Econo-pack column and the beads were trapped on the bottom of the column so as to collect the supernatant containing the tag-free RBD. The supernatant was then subjected to an additional buffer exchange, to reduce the NaCl concentration below 5 mM. The solution from previous step was loaded on Q-sepharose beads from Bio-works pre-equilibrated with 10 mM PO4 pH 7.4 buffer. The flow-through was collected and analyzed by SDS-PAGE shown in FIG. 3B.

Example 4: RBD Protein Identification by Western Blot

Figure 4:
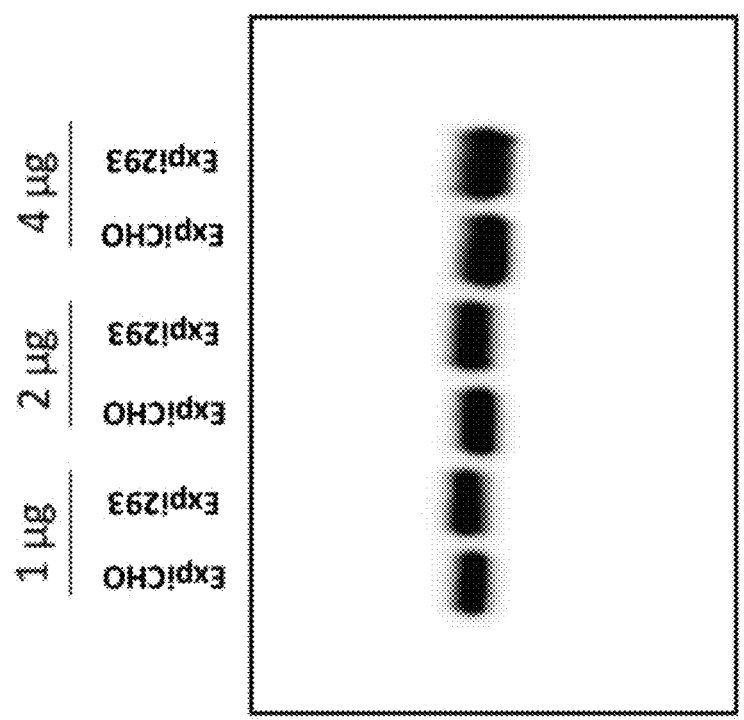
FIG. 4 depicts the western blot results showing the purified samples of the RBD CoV-S polypeptide of SEQ ID NO: 1 produced in ExpiCHO and Expi293 cells identified by anti-RBD antibody.

A western blot was performed to establish the correct identity of the protein expressed in the example 3. The following reagents were prepared: lx Transfer buffer (20% of Ser. No. 10/026,938 Trans-Blot Turbo 5× Transfer Buffer (Bio-Rad), 20% ethanol with 60% purified water); lx Tris-buffered saline with Tween-20 (TBST) for washing buffer (20 mM Tris, 500 mM sodium chloride, pH 7.5 and 0.1% tween-20); Blocking buffer (3% BSA or milk powder solution); Primary antibody solution (#AE003 Mouse Anti His-tag mAb (Abclonal)); Secondary antibody solution (#AS003 HRP Goat Anti-mouse igG (Abclonal)); Clarity™ Western ECL Substrate (#170-5061 (Bio-Rad)). An SDS-PAGE was performed for the purified recombinant RBD, then the recombinant proteins were transferred from the SDS-PAGE gel to a LF PVDF membrane, previously activating with ethanol for 1 minute and rinsed with transfer buffer before preparing the stack. Then the stack was inserted in a Trans-blot Turbo Transfer System (Bio-Rad). Before the blocking step, a Ponceau S staining was performed in order to verify the transfer efficiency of the proteins to the membrane. Then, the membrane was blocked by the blocking buffer for 1 hour at room temperature, followed by incubating with a ⅕₀₀₀× dilutions of primary antibody in blocking buffer for 2 hours at room temperature. Afterwards, the membrane was washed in TBST for 5 times and 5 minutes each. After the washing step, the membrane was incubated with a ⅕₀₀₀×dilution of conjugated secondary antibody in blocking buffer at room temperature for 1 hour. Then the membrane was washed again in TBST for 5 times and 5 minutes each so as to remove the excess reagents. The membrane was packed in transparent plastic wrap to acquire the image via a Chemi-Doc MP Imaging System shown in FIG. 4.

Example 5: Full Removal of the Purification Tag from the Purified RBD

Figure 5B:
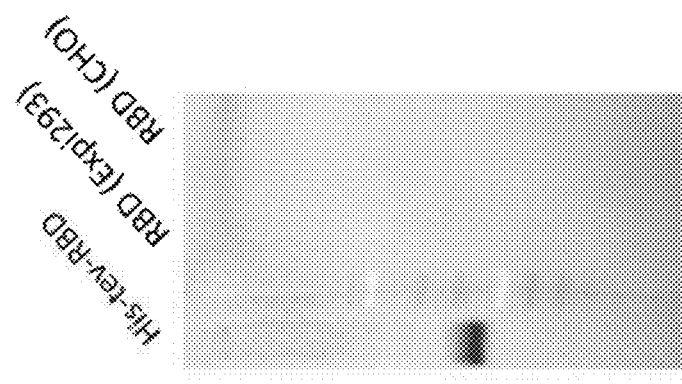
FIG. 5B depicts the western blot of the purified samples of the TEV treated RBD-CoV-S polypeptide of SEQ ID NO: 1 produced in ExpiCHO and Expi293 cells identified by anti-histag-antibody.
Figure 5A:
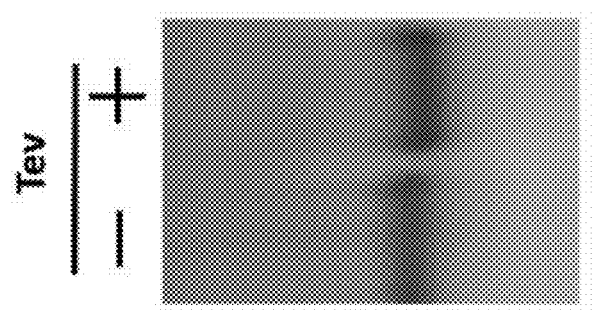
FIG. 5A illustrates the electrophoresis results of the purified samples of the RBD-CoV-S polypeptide of SEQ ID NO: 1 before (−) and after (+) the treatment with the TEV protease for the removing of the 6×-histidine-tags.

To assess the completely removal of the six histidine tag from the purified RBD protein, a Western Blot was performed with the RBD produced in ExpiCHO and Expi293 cells. Most of the procedures for the Western Blot was similar as described in the example 4, except for the use of anti-histag antibody as primary antibody. As shown in FIGS. 5A and 5B, the six histidine tag has been removed successfully from the RBD samples.

Example 6: Glycosylation Profile of the Produced RBD

Furthermore, a nano LS-MS/MS analysis was performed to identify the glycosylation profile of the produced RBD protein. 200 μg of the purified RBD was subjected to protein hydrolyzation and the detailed procedures are as follows: Sample Preparation: (1) DTT solution was added to a final concentration of 10 mmol/L, and reduced in a 56° C. water bath for 1 h; (2) IAA solution was added to a final concentration of 50 mmol/L and protect from light for 40 min; (3) Enzyme was added into the protein solution and then incubated at 37° C. overnight; (4) After digestion, the peptide was desalted via a self-priming desalting column, and the solvent was evaporated in a vacuum centrifuge at 45° C.; (5) The peptide was dissolved in the sample solution (0.1% formic acid, 2% acetonitrile), vortexed thoroughly, centrifuged at 13200 rpm for 10 min at 4° C., and the supernatant was transferred to the sample tube for mass spectrometry analysis. The parameters for the LC-MS/MS analysis are shown in Table 1.

TABLE 1

Parameters for nano LC-MS/MS analysis

Nano liquid chromatography*

| | |
|---|---|
| System | Nanoflow UPLC: Easy-nLC1000 (ThermoFisher Scientific, USA) |
| Nanocolumn | 100 μm × 10 cm in-house made column packed with a reversed-phase ReproSil-Pur C18-AQ resin (3 μm, 120 Å, Dr. Maisch GmbH, Germany) |
| Mobile phase | A: 0.1% formic acid in water; B: 0.1% formic acid in acetonitrile. Total flow rate: 600 nL/min |
| LC linear gradient | from 6% to 9% B for 8 min, from 9% to 14% B for 16 min, from 14% to 30% B for 36 min, from 30% to 40% B for 15 min and from 40% to 95% B for 3 min, eluting with 95% B for 7 min. |

TABLE 1-continued

Parameters for nano LC-MS/MS analysis

Mass Spectrometry

| System | Q Exactive ™ Hybrid Quadrupole-Orbitrap ™ Mass Spectrometer (Thermo Fisher Scientific, USA) |
|---|---|
| Spray voltage: 2.2 kV | Capillary temperature: 270° C. |

MS parameters:
MS resolution: 70000 at 400 m/z;
MS precursor m/z range: 350.0-1800.0
MS/MS parameters:
Product ion scan range: start from m/z 100; Activation Type: CID;
Min. Signal Required: 1500.0; Isolation Width: 3.00; Normalized Coll.
Energy: 40.0; Default Charge State: 6; Activation Q: 0.250;
Activation Time: 30.000; Data dependent MS/MS: up to top 15
most intense peptide ions from the preview scan in the Orbitrap

*the sample loading volume was 5 µl

The raw MS files were analyzed and searched against protein database based on the species of the samples via Byonic. The parameters were set as follows: the protein modifications were carbamidomethylation (C) (fixed), oxidation (M) (variable), Acetyl(Protein N-term)(variable); the enzyme specificity was set to trypsin or chymotrypsin or trypsin and Glu-C; the maximum missed cleavages were set to 3; the precursor ion mass tolerance was set to 20 ppm, and MS/MS tolerance was 0.02 Da. Only high confident identified peptides were chosen for downstream protein. The results are shown in FIG. 6, which demonstrates how the coronavirus Receptor Binding Domain (RBD) of the Spike protein (S)(SEQ ID NO: 1) shows a correct glycosylation profile, where there are two N-glyco groups (residue N331 and N343) and one O-glyco group (residue T323) in the RBD protein produced by ExpiCHO cell, and two N-glyco groups (residue N331 and N343) in the RBD protein produced by Expi293 cell.

Figure 7:
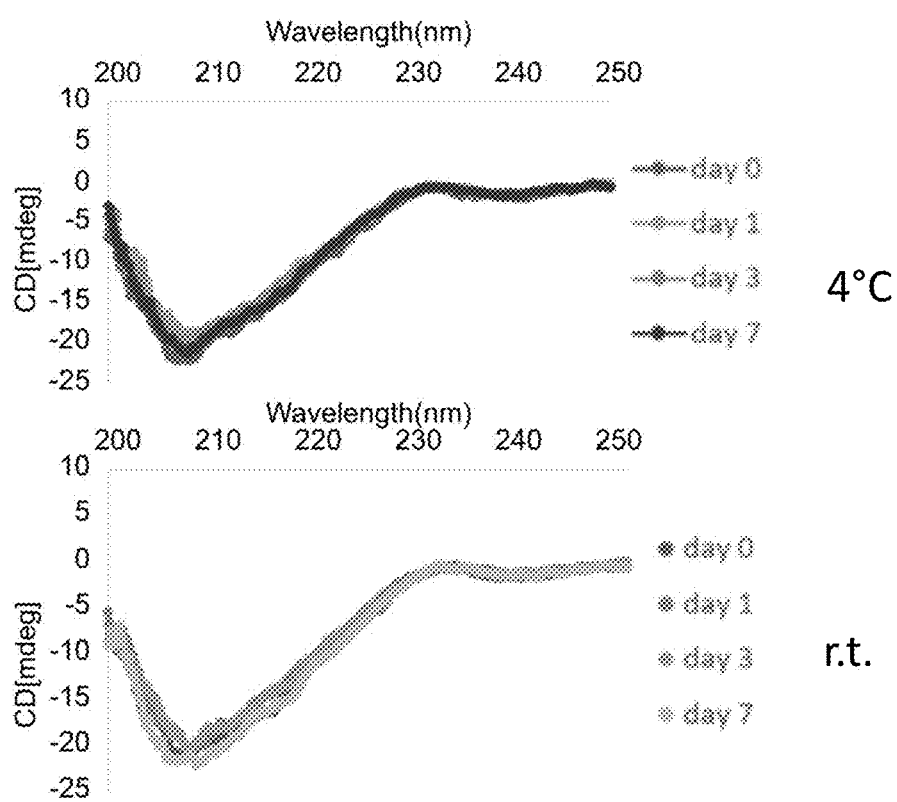
FIG. 7 depicts the CD spectra of the recombinant RBD of SEQ ID NO: 1 purified from ExpiCHO cells at storage temperature 4° C. and room temperature.

Example 7: Determination of the Stability of the Secondary Structure of the Produced RBD Protein as Function of the Storage Temperature Several aliquots of 300 µl with a 10 µM solution of the purified coronavirus Receptor Binding Domain (RBD) of the Spike protein (S) of SEQ ID NO: 1 from ExpiCHO Cells in phosphate buffer 10 mM pH 7.2 were prepared. Four tubes were stored at room temperature and the other tubes were kept at 4° C. The solutions were loaded into a quartz cuvette with a 1 mm path length. The samples were analyzed by circular dichroism (CD) Spectroscopy by a JASCO J-1500 Circular Dichroism Spectrophotometer. Circularly polarized light consists of both left- and right-handed direction. The chiral chromophores on a molecule preferentially absorb one of the directions of the light. Therefore, based on the differential absorption of left and right circularly polarized light, the stereochemical information of the RBD protein can be obtained. Moreover, analyzing at different time points (0, 1, 3 and 7 days) is able to evaluate the stability of the RBD recombinant protein as function of the storage temperature. Referring to FIG. 7, it clearly illustrates the produced RBD recombinant protein is able to maintain and conserve a stable secondary structure over all time window.

Example 8: Research and Application of the pIRES2_RBD_eGFP for Producing the SARS-CoV-2 Coronavirus Antigen (RBD SARS_CoV-2) and Inducing a Specific Immune Response to SARS-CoV-2

The compositions in the present invention may include suitable adjuvants, stabilizers, excipients and the claimed coronavirus Receptor Binding Domain (RBD) of the Spike protein (S)(i.e., SEQ ID NO: 1) as antigen. Induction of a specific immune response to SARS-CoV-2 antigens is provided by administrating into the human or animal subject with the immunogenic compositions based on the RBD recombinant protein in the present invention, by any of the known methods, for example but not limited to intramuscularly, intravenously, or subcutaneously. The immunogenic investigations of the produced recombinant RBD protein were performed by a triple subcutaneous immunization of mice.

The composition comprising the coronavirus Receptor Binding Domain (RBD) of the Spike protein (S)(i.e., SEQ ID NO: 1) as described in example 1 was evaluated for immunogenicity in a murine model by using female BALB/c mice (7-9 weeks old, Ecozoo Lab, Italy.). The preferred composition for the investigation is as: (1) recombinant coronavirus RBD polypeptide antigen produced from Expi293 Cells (30 µg and 50 µg dosages); and (2) Recombinant coronavirus RBD polypeptide antigen produced from ExpiCHO Cells (30 µg and 50 µg dosages) and the detailed procedures for the preparation of vaccine composition are as follows: (1) Prepare the antigen and PBS mixture. Since the final volume of the mixture was 50 µl, which includes 29.7 µl of antigen solution and 20.3 µl PBS (pH 7.2). The volume of the required antigen solution was calculated by the below equation:

$$\text{The volume of antigen for injection}(\mu l) = \frac{\text{Amount need for injection}}{\text{Antigen solution concentration}}$$

Therefore, the volume of antigen for injection was 29.7 µl while the amount need for injection was 30 µg and the antigen solution concentration was 1.01 mg/ml. (2) the tube with Alhydrogel adjuvant 2% was mixed well before use; (3) Added Alhydrogel adjuvant 2% to the mixture from step (1) and the final volume ratio of Alhydrogel adjuvant 2% to the antigen and PBS mixture is 1:1 (i.e., 50 µl Alhydrogel adjuvant 2% for 50 µl of antigen+PBS mixture). (4) Mixed thoroughly by pipetting up and down for at least 5 minutes such that Alhydrogel adjuvant 2% is able to effectively adsorb the antigen. The vaccine composition should be kept at room temperature during this step. (5) Take 100 µl vaccine composition from step (4) and prepare for further injection to mice.

The mice were applied with the composition in the presence and in the absence of an Alumn adjuvant, e.g., Alhydrogel adjuvant 2%. The investigation comprises one negative control group without receiving any treatment, one group treated with adjuvant+PBS, and one group with only PBS. Furthermore, the test system housing was configured as follows: each treatment group was housed in cage under 12 hours of artificial light and 12 hours of dark cycle, in a livestock housing with a limited access. Water was supplied ad libitum by drinking bottles, and feed was administered ad libitum by stainless feeder.

Figure 8:
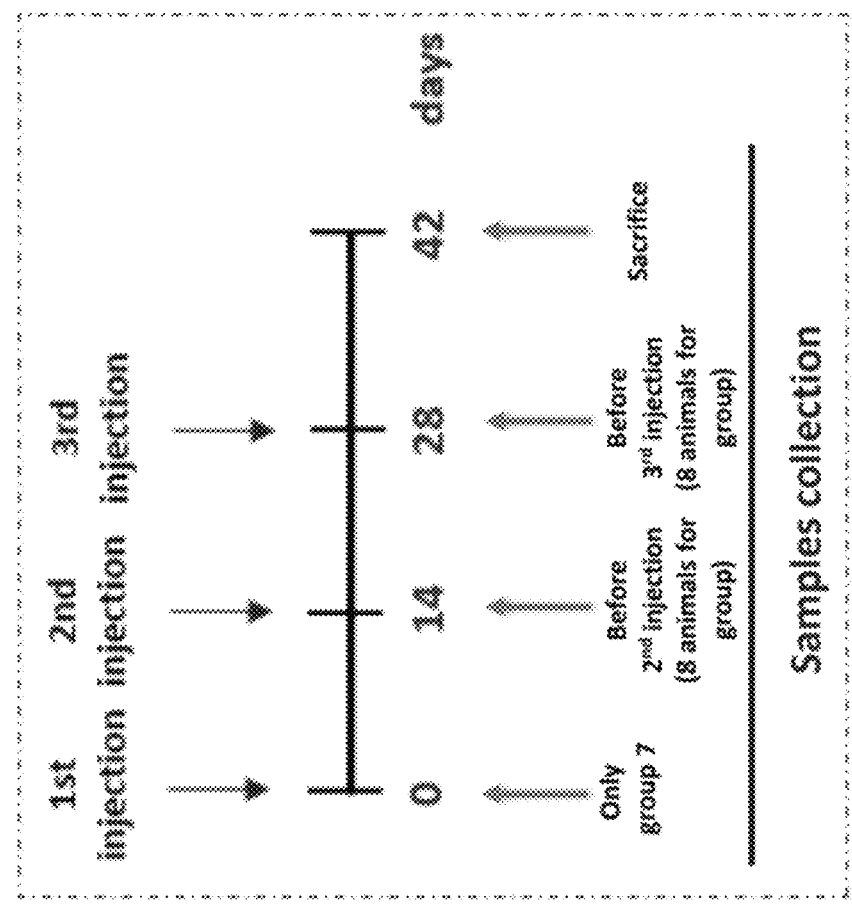
FIG. 8 depicts the schematic of the dosage time interval and experimental procedures for the animal study.

As shown in FIG. 8 and table 2, vaccine compositions containing recombinant coronavirus RBD polypeptide at various amounts of 30 µg and 50 were administered subcutaneously as triple doses (0, 14 and 28 days). Meanwhile, a placebo group served as a non-immunized control with PBS. Physical observations, including visual check on general appearance of the mice (e.g., fur and activity levels/responsiveness), for health status was conducted daily. Particularly attention was paid to the injection site for the presence of any reactions to the treatment. Body weights and feed intakes was measured before administration (Day 0) and then weekly till the end of the study. Then, serum was collected for further analysis of immunogenicity on days 0, 14, 28, and 42. The serum of the mice was collected at 4 time points: Day 0 (from 4 mice in group 7), Day 14, Day 28 (8 mice/group 1, 2, 3, and 4; 4 mice/group 5, 6 and 7) and Day 42 (all mice; terminal/end of in-life) to assess antibody responses.

TABLE 2

A summary of the dosage and the animal number for each group

| Group ID | Formulation | Antigen Dose | Administered Volume | Administration days | Rout of administration | No. Animals |
|---|---|---|---|---|---|---|
| 1 | RBD from Expi293 Cell + Alumn + PBS | 30 µg | 100 µl | 0-14-28 | SC | 22 |
| 2 | RBD from Expi293 Cell + Alumn + PBS | 50 µg | 100 µl | 0-14-28 | SC | 22 |
| 3 | RBD from ExpiCHO Cell + Alumn + PBS | 30 µg | 100 µl | 0-14-28 | SC | 22 |
| 4 | RBD from ExpiCHO Cell + Alumn + PBS | 50 µg | 100 µl | 0-14-28 | SC | 22 |
| 5 | Alumn + PBS | N.A. | 100 µl | 0-14-28 | SC | 4 |
| 6 | PBS | N.A. | 100 µl | 0-14-28 | SC | 4 |
| 7 | No treatment | N.A. | N.A. | N.A. | N.A. | 4 |

Among the non-terminal intervals, the blood was collected from the cheek and the mice were slightly anesthetized by isofluorane to avoid stress during the sampling procedure. As for terminal blood collection, mice were anesthetized by isofluorane then sacrificed by cervical dislocation and undergo cardiac puncture and the maximum blood volume was collected via exsanguination. The volume for blood collection during in-life phase was 80-100 µl and 800 µl during terminal bleeding via cardiac puncture. Serum was obtained from the whole blood placed in the tubes by centrifugation and the serum was stored in cryovials at −20° C. Meanwhile, no pathological changes were found in the heart, brain, liver, spleen, lung, kidney and other organs as well as no changes in blood cells and blood biochemical indicators were found at the end of the study the animals were sacrificed.

Vaccine Immunogenicity—Mice IgG1 RBD-Specific ELISA Assay

To perform the RBD-IgG1 ELISA, ELISA plates were firstly coated with 1 µg/mL of purified recombinant Receptor-Binding domain (RBD) HEK-derived protein (Sino Biological, Beijing, China) and incubated overnight at 4° C. The RBD polypeptide was synthesized according to the sequence of SARS-CoV-2 2019 (Wuhan), the B.1.351 (South Africa variant) and B.1.617.2 (Delta) by Sino Biological (China). The polypeptide sequences for those RBDs are as follows:

RBD SARS-CoV-2 (wild-type, Wuhan-1):
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYLYRLFRKSNLKPFERDIST

EIYQAGSTPCNGVEGFNCYFPLQSYGFQPTNGVGYQPYRVVVLSFELLHAP

ATVCGPKKSTNLVKNKCVNF

B.1.351 (Beta variant):
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGNIAD

YNYKLPDDFTGCVIAWNSNNLDSKVGGNYNYLYRLFRKSNLKPFERDIST

EIYQAGSTPCNGVKGFNCYFPLQSYGFQPTYGVGYQPYRVVVLSFELLHA

P ATVCGPKKSTNLVKNKCVNF

B.1.617.2 (Delta variant):
RVQPTESIVRFPNITNLCPFGEVFNATRFASVYAWNRKRISNCVADYSVLY

NSASFSTFKCYGVSPTKLNDLCFTNVYADSFVIRGDEVRQIAPGQTGKIAD

YNYKLPDDFTGCVIAWNSNNLDSKVGGNYNYRYRLFRKSNLKPFERDIST

EIYQAGSKPCNGVEGFNCYFPLQSYGFQPTNGVGYQPYRVVVLSFELLHA

PATVCGPKKSTNLVKNKCVNF

After overnight incubation, the coated plates were washed three times with 300 µL/well of ELISA washing solution containing Tris Buffered Saline (TBS)-0.05% Tween 20, then saturated for 1 hour at 37° C. with a solution of TBS containing 5% of Non-Fat Dry Milk (NFDM; Euroclone, Pero, Italy). The mice serum from example 8 were conducted with 2-fold serial dilution, starting from 1:100 in TBS-0.05% Tween 20 and 5% NFDM, up to 1:51200. The plates were washed three times and then 100 µL of each serial dilution was transferred to the coated plates and incubated for 1 hour at 37° C. Next, after the washing step, 100 µL/well of Goat anti-Mouse IgG1 Horse Radish Peroxidase (HRP)-conjugated antibody with 1:50,000 (Bethyl Laboratories, Montgomery USA) dilution was added into the plates and incubated at 37° C. for 30 min. Following incubation and subsequent washing step, 100 µL/well of 3,3',5,5'-Tetramethylbenzidine (TMB) substrate (Sigma-Aldrich) was added and incubated in the dark at room temperature for 20 min. The reaction was stopped by adding 100 µL of 0.18 M $H_2SO_4$ solution (Fisher Scientific cod. 10080210) and analyzed in the ELIZA reader at 450 nm (Spectramax, Medical Device).

Figure 9:
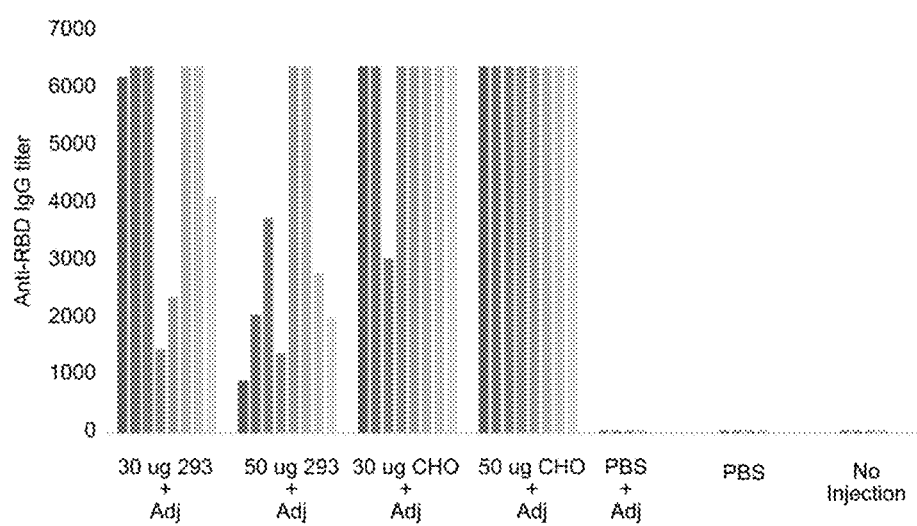
FIG. 9 depicts the titers of the anti-RBD IgG in the samples collected from the mice blood after 14 days of the $1^{st}$ immunization, where the RBD protein coated on the ELISA plate was from the wild-type strain (Wuhan-1) of SARS-CoV-2 coronavirus.
Figure 10:
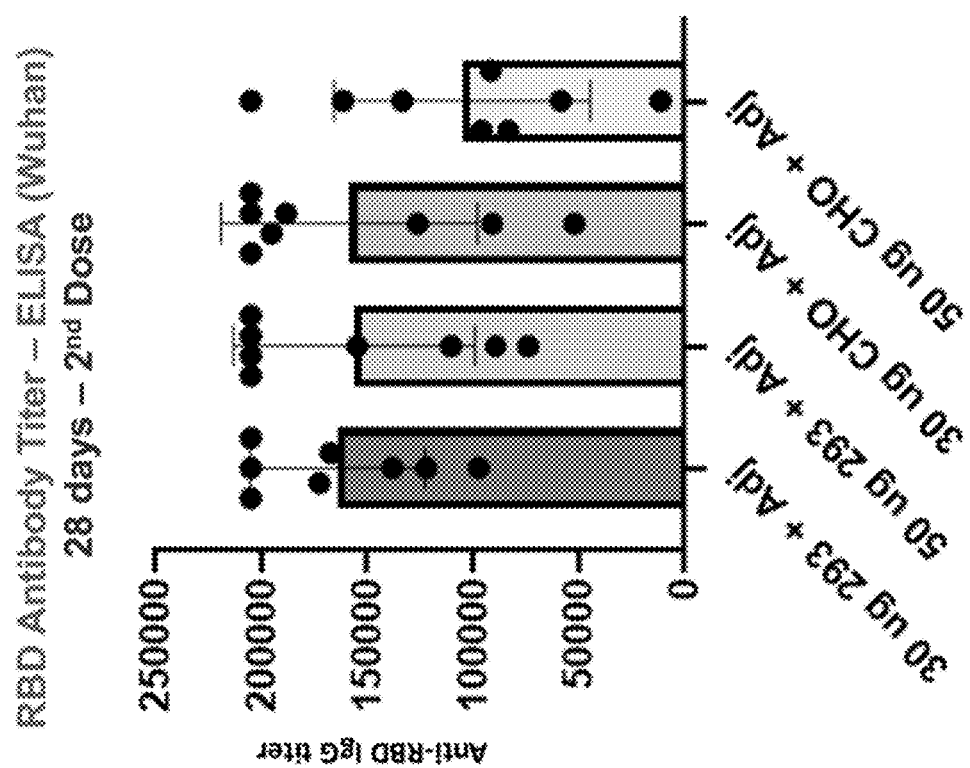
FIG. 10 depicts the titers of the anti-RBD IgG in the samples collected from the mice blood after 14 days of the $2^{nd}$ immunization, where the RBD protein coated on the ELISA plate was from the wild-type strain (Wuhan-1) of SARS-CoV-2 coronavirus.
Figure 11:
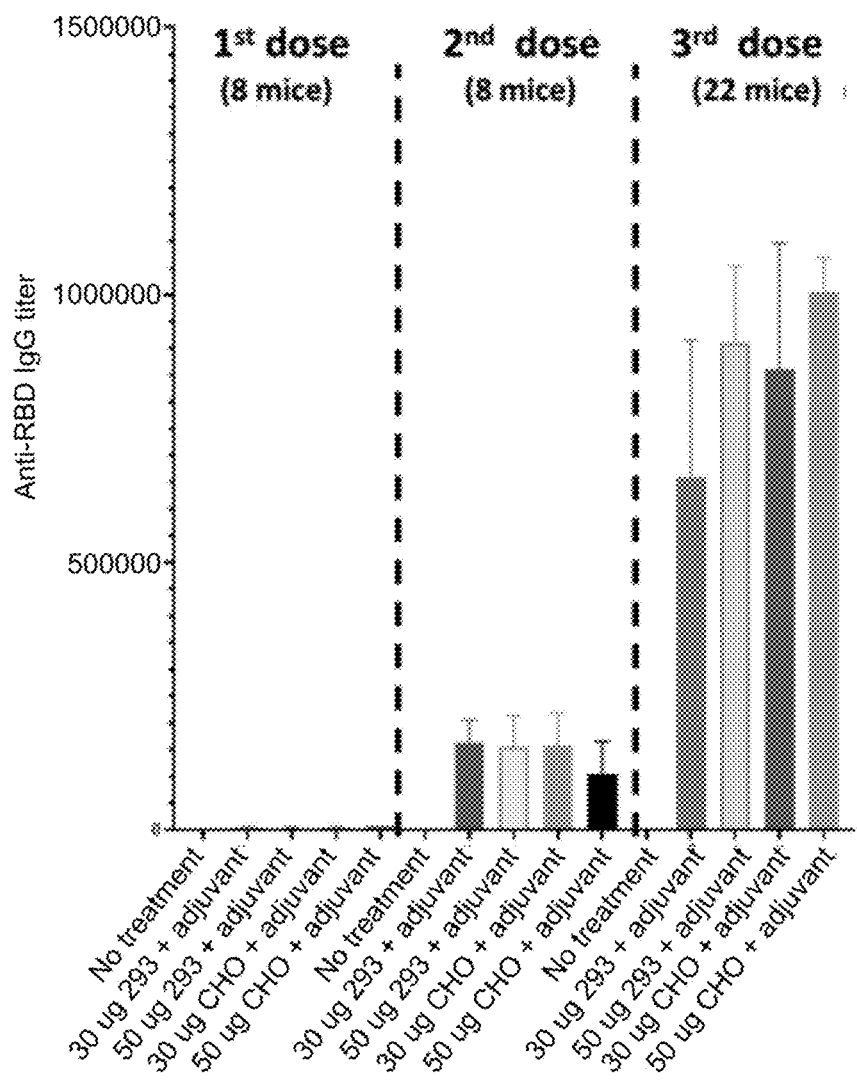
FIG. 11 illustrates the summary of the titers of the anti-RBD IgG in the samples collected from the mice blood after $1^{st}$, $2^{nd}$, and $3^{rd}$ immunization, where the RBD protein coated on the ELISA plate was from the wild-type strain (Wuhan-1) of SARS-CoV-2 coronavirus.
Figure 12:
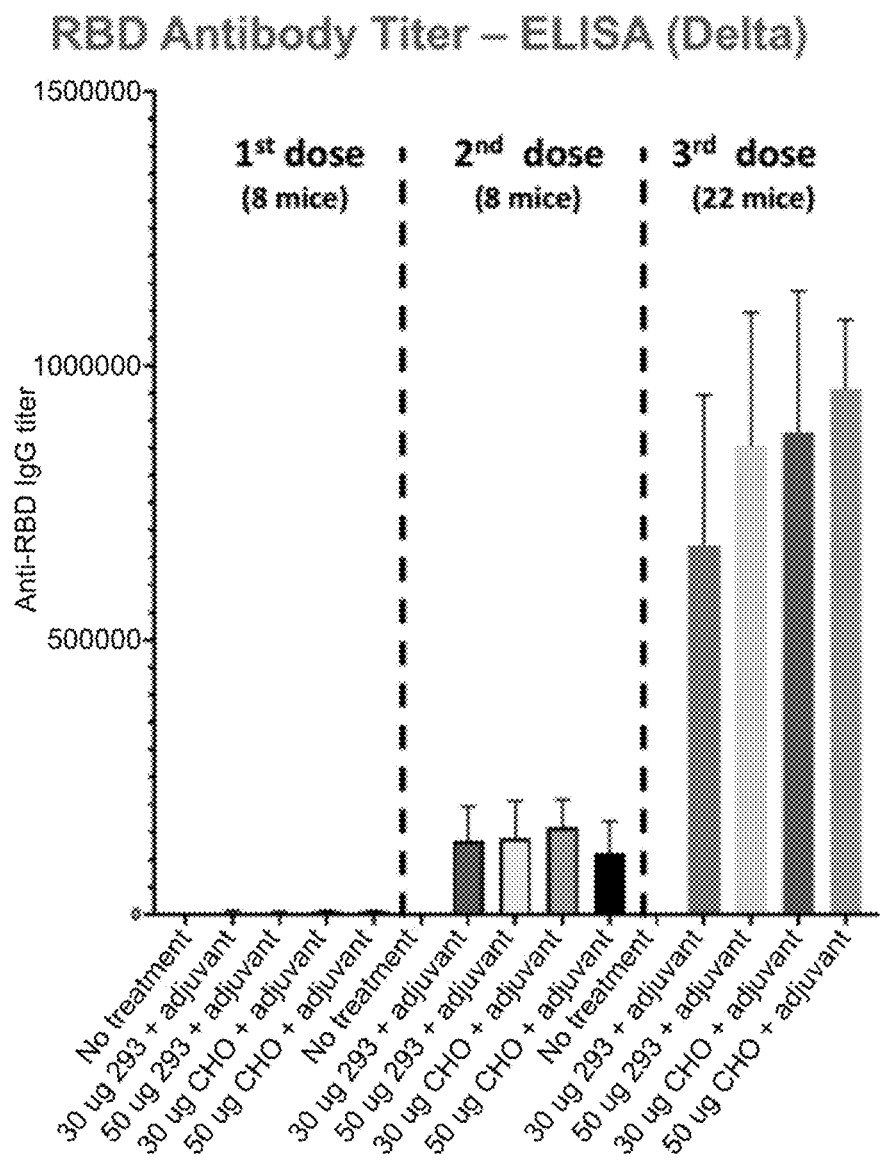
FIG. 12 illustrates the summary of the titers of the anti-RBD IgG in the samples collected from the mice blood after $1^{st}$, $2^{nd}$ and $3^{rd}$ immunization, where the RBD protein coated on the ELISA plate was from the B.1.617.2 strain (delta) of SARS-CoV-2 coronavirus.
Figure 13:
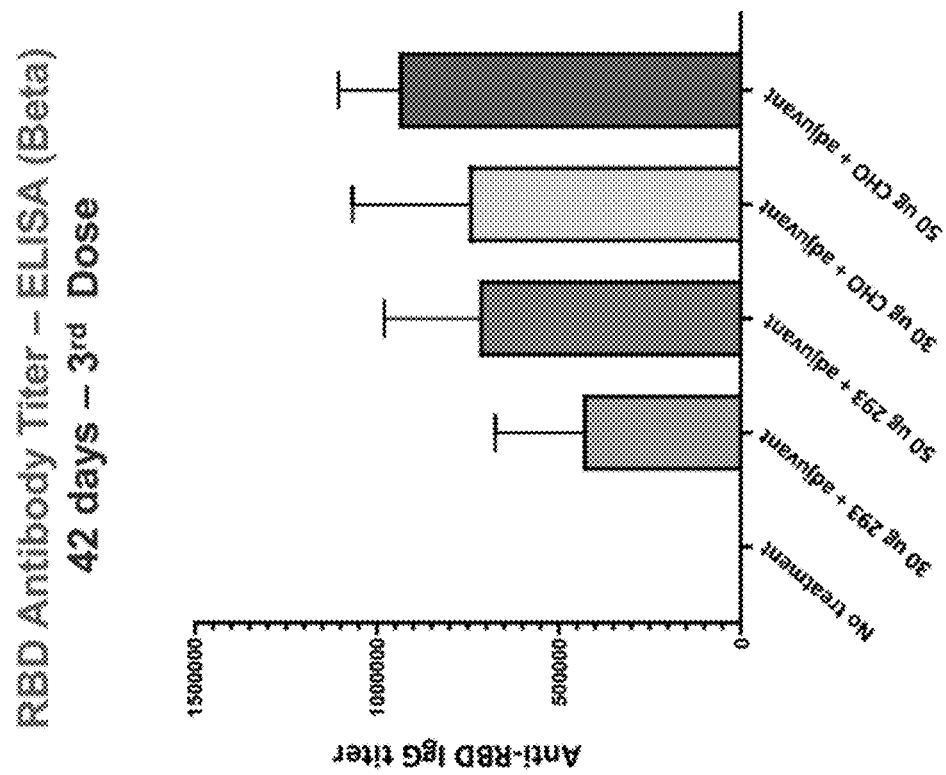
FIG. 13 depicts the titers of the anti-RBD IgG in the samples collected from the mice blood after 14 days of the $3^{rd}$ immunization, where the RBD protein coated on the ELISA plate was from the B.1.351 strain (Beta) of SARS-CoV-2 coronavirus.

The positive control was applied with anti-RBD mouse IgG monoclonal antibodies starting from 1:8000 dilution in each ELISA plate (Native Antigen, Oxford, UK). As show in FIG. 9, animals immunized with one dose of 30-50 µg recombinant RBD polypeptide of SEQ ID NO: 1 from both the cell lines (i.e., Expi293 and ExpiCHO cell lines) and Alumn developed an anti-RBD IgG titers that were detected 14 days after the first immunization. The titer of IgG RBD-specific antibodies in the blood serum of mice in all the groups including the antigen was at least 1:5000. Animals immunized with the prime/boost regimen (two doses) had significantly elevated anti-RBD IgG titers that were detected 14 days following the second immunization across all dose levels shown in FIG. 10. The titer of IgG RBD-specific antibodies in the blood serum of mice in all the groups including the antigen was at least 1:100000. Furthermore, animals immunized with a triple dose had very high anti-RBD IgG titers following 14 days after the third immunization shown in FIG. 11. The titer of IgG RBD-specific antibodies in the blood serum of mice in all the groups including the antigen was at least 1:600000. As shown in FIG. 12 and FIG. 13, the similar high anti-RBD IgG titers were identified for the ELISA test by using the RBD from the B.1.617.2 strain (Delta) and B.1.351 strain (Beta), respectively.

Vaccine Immunogenicity—Micro-Neutralization Assay CPE-Based

The Micro-Neutralization assay was performed according to Manenti et al. 2020. Briefly, 2-fold serial dilutions of heat-inactivated mice serum samples were mixed with an equal volume of viral solution containing between 25-100 TCID50 of SARS-CoV-2 to obtain the mixture of serum and virus. The mixture was then incubated for 1 hour at 37° C. in a humidified atmosphere with 5% $CO_2$. After the incubation, 100 µL of the mixture at each dilution was transferred to a 96-well plate containing a sub-confluent (75-85%) VERO E6 (ATCC-CRL 1586) monolayer. The plates were incubated for 3 days (Wild type strain, Wuhan-1) and for 4 days (B.1.351, B.1.617.2 and B1.1.529 (Omicron) at 37° C. in a humidified atmosphere with 5% $CO_2$. Then, the plate was investigated by means of an inverted optical microscope to evaluate the percentage of cytophatic effect (CPE) developed in each well and the neutralization titer has been considered as the reciprocal of the highest dilution of serum able to inhibit and prevent at least 50% of cells with CPE.

The SARS-CoV-2 2019-nCov/Italy-INMI1 clade V (Wuhan) and the B.1.351 (Beta variant) named Human nCoV19 isolate/England ex-SA/HCM002/2021 were both purchased from Europen Virus Archive (EVAg), B.1.617.2 (Delta) and B1.1.529 (Omicron) were isolated by VisMederi. SARS-CoV-2 strains were propagated in VERO E6 cells (ATCC-CRL 1586) in T175 Flasks by using Dulbecco's Modified Eagle's—high glucose medium (DMEM) (Euroclone, Pero, Italy) supplemented with 2 mM L-glutamine (Lonza, Milano, Italy), 100 units/mL penicillin-streptomycin (Lonza, Milano, Italy and 2% fetal bovine serum (FBS) (Euroclo, Pero, Italy). All viral growth and neutralization assay with SARS-CoV-2 live viruses were performed inside the VisMederi Biosafety Level 3 laboratories.

Figure 14:
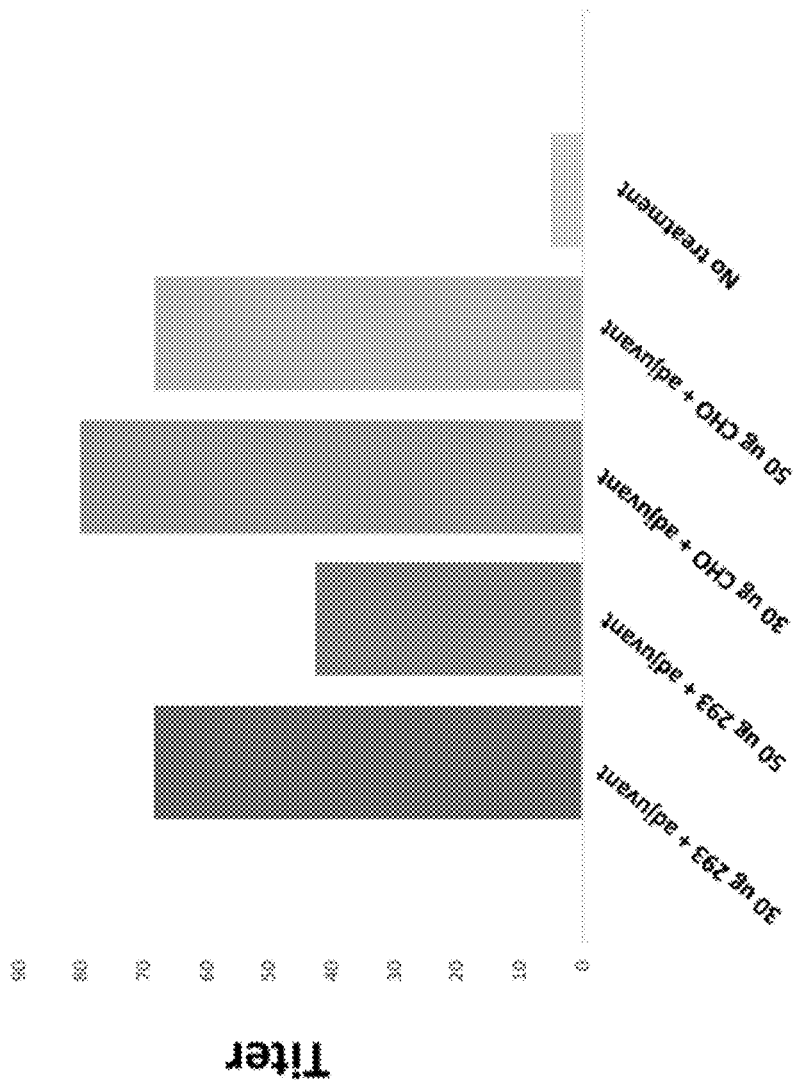
FIG. 14 illustrates the titers of the neutralizing antibodies from the mice serum after 14 days of the $2^{nd}$ immunization obtained by a Micro Neutralization assay with live virus. The strain utilized for this assay was the SARS-CoV-2 2019-nCov/Italy-INMI1 clade V (Wuhan-1).
Figure 15:
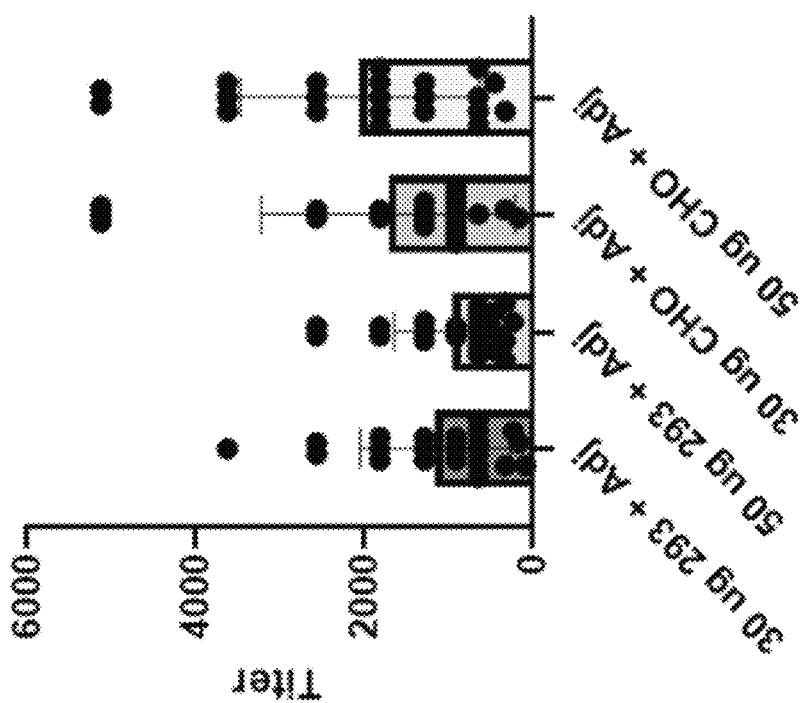
FIG. 15 illustrates the titers of the neutralizing antibodies from the mice serum after 14 days of the $3^{rd}$ immunization obtained by a Micro Neutralization assay with live virus. The strain utilized for this assay was the SARS-CoV-2 2019-nCov/Italy-INMI1 clade V (Wuhan-1).

As shown in FIG. 14, it has been identified that mice immunized with a dose containing 30 µg or 50 µg of the recombinant RBD from both cell lines and Alumn were able to produce neutralizing antibodies to block hACE2 receptor binding to the CoV Spike protein on 28 days after the prime/boost regiment (two doses). The titer of IgG neutralizing RBD-specific antibodies in the blood serum of mice in all the groups including the antigen was at least 1:50. Furthermore, as shown in FIG. 15, animals immunized with a triple dose had very high neutralizing anti-RBD IgG titers following 14 days after the last immunization. The titer of neutralizing IgG RBD-specific antibodies in the blood serum of mice in all the groups including the antigen was at least 1:1500. The similar trend was identified against all four SARS-CoV-2 virus variants tested and shown in FIG. 16 and FIG. 17.

Vaccine Immunogenicity—T Cell Response

The effect of the vaccine composition comprising a coronavirus Receptor Binding Domain (RBD) of the Spike protein (S)(SEQ ID NO: 1) on the T cell response was also evaluated. The BALB/c mice (N=4 per group) were immunized intramuscularly with 30-50 µg RBD with an equal volume of Alumn for 3 doses in 14-days interval. Spleens were collected 14-days after the third immunization (i.e., day 42). A non-vaccinated group (N=2), a group treated with Alumn+PBS (N=2), and a group with only PBS(N=2), were regarded as control groups.

Figure 20:
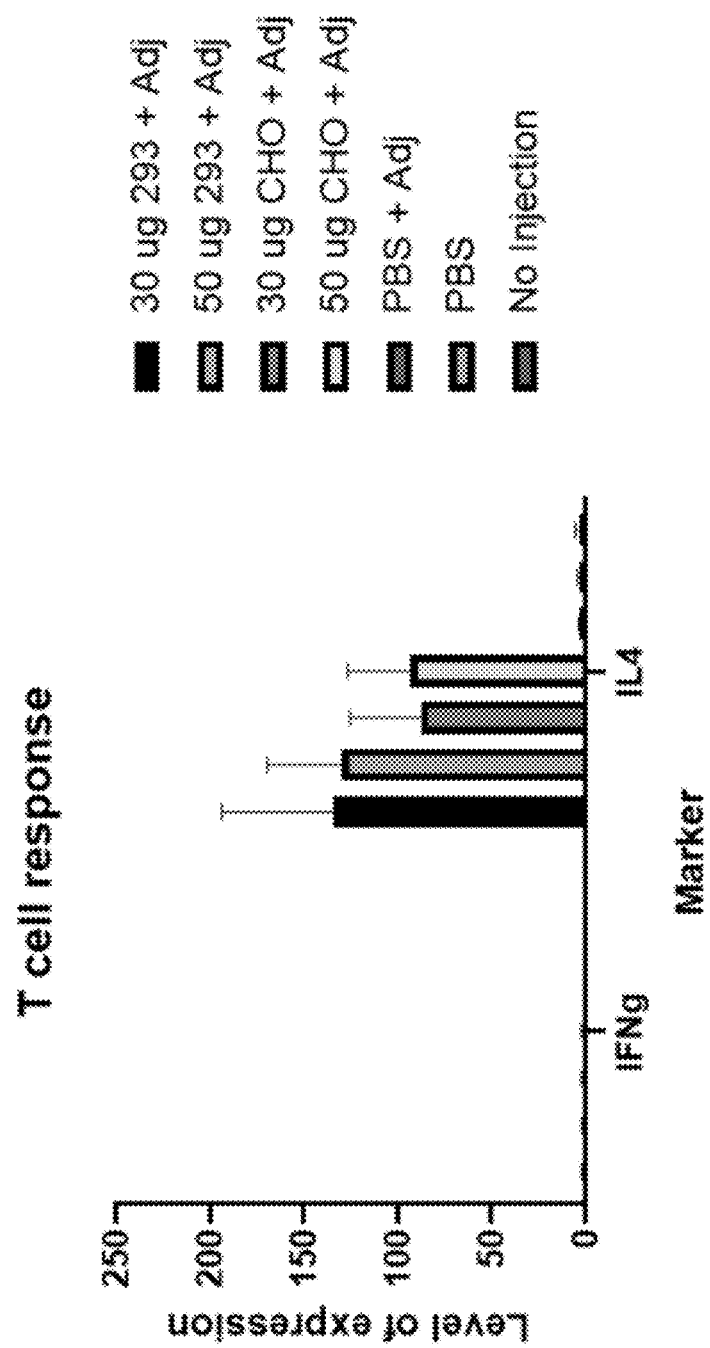
FIG. 20 depicts the summary for the Th1/Th2 response after immunizing the mice with RBD and Alumn.

Antigen-specific T cell responses were measured by ELISPOT™ enzyme linked immunosorbent assay and intracellular cytokine staining (ICCS) from spleens collected 14-days after the third immunization (day 42). As shown in FIG. 18, the Th1 response was evaluated by identifying the number of IFN-γ secreting cells after ex vivo stimulation in spleens of mice immunized with the recombinant RBD and Alumn compared to the control groups by the ELISPOT™ assay. As shown in FIG. 19, the Th2 response was evaluated by identifying the number of IL-4 secreting cells after ex vivo stimulation in spleens of mice immunized with the recombinant RBD and Alumn compared to the control groups by the ELISPOT™ assay. The results of the Th1 and Th2 responses are compared and analyzed in FIG. 20, where a prevalent Th2 response over Th1 response in all the mice immunized with a dose containing 30-50 µg RBD from both cell lines and Alumn was observed. In the light of all these results suggest an immunogenic composition based on the claimed RBD (SEQ ID NO: 1) with an adjuvant can be considered as an effective vaccine composition candidate for protecting humans and animals from COVID-19 coronavirus infection (SARS-CoV-2).

In summary, the present invention provides (1) less risk of endotoxin contaminations than the RBD produced in *E. coli*; (2) Express higher protein yield in less time, resulting in less labor and other costs (plasticware and reagents); (3) Beneficial balance between speed, cost and safety of the production compared to other expression systems; (4) The system provides a large amount of proteins with consistent quality and regulatory familiarity; (5) The serum-free medium reduces risk of animal component-associated infections as the has been medium adapted to be animal-origin-free to ensure patient safety. The demand for animal-origin free culture medium has been at the forefront of many biopharmaceutical companies in terms of drug development and production; (6) The ability to maintain constitutive expression and high yield of the protein under animal-origin free conditions is therefore highly desirable; (7) The high synergy between the expression vector and the cell line allows for a high production of RBD protein; and (8) The fact that the RBD is produced in mammalian cell guarantees for the correct folding of the protein for human use; (9) The Vaccine formulation based on this invention can be stored at very convenient temperature; and (10) The Vaccine formulation based on this invention can elicit very high titer of neutralizing antibodies against SARS-CoV-2 strains.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

The invention claimed is:

1. An expression vector for producing a recombinant SARS-CoV-2 polypeptide or fragment thereof, comprising:
   at least one polynucleotide sequence encoding at least one signal peptide sequence;
   one or more polynucleotide sequences encoding one or more affinity tags;
   at least one polynucleotide sequence encoding a protease recognition site sequence;
   one or more polynucleotide sequences encoding one or more reporter sequences; and
   a polynucleotide sequence encoding a receptor-binding domain (RBD) sequence of SARS-CoV-2 spike glycoprotein that is at least 80 percent identical to SEQ ID NO. 2;
   wherein the recombinant polypeptide is formed in bicistronic structure;
   wherein the polynucleotide sequence encoding the protease recognition site sequence is positioned between the polynucleotide sequence encoding the affinity tag and the polynucleotide sequence encoding the receptor-binding domain sequence such that a protease cleaves the affinity tag from the RBD sequence of SARS-CoV-2 spike glycoprotein to create a tag-free RBD sequence; and
   wherein the polynucleotide sequence further includes a polynucleotide sequence for an internal ribosome entry site operatively linked between the receptor-binding domain (RBD) polynucleotide sequence and the reporter polynucleotide sequence.

2. The expression vector of claim 1, wherein the signal peptide sequence is selected from human serum albumin, human granulocyte colony-stimulating factor or combination thereof.

3. The expression vector of claim 1, wherein the affinity tag is selected from chitin binding protein, maltose binding protein, streptavidin, poly histidine, or combination thereof.

4. The expression vector of claim 1, wherein the protease recognition site sequence can be recognized by a tobacco etch virus protease.

5. The expression vector of claim 1, wherein the reporter sequence is selected from enhanced yellow fluorescent protein, enhanced red fluorescent protein, enhanced green fluorescent protein, beta-galactosidase, or combination thereof.

6. The expression vector of claim 1, wherein the expression vector further comprises one or more nucleotide signal sequence selected from SV40 poly(A) nucleotide sequences, HSV TK poly(A) nucleotide sequences, or combination thereof.

7. The expression vector of claim 1, wherein the expression vector further comprises one or more polynucleotide sequences encoding a promoter sequence selected from SV40 promoter, ampR promoter, CMV promoter or a combination thereof.

8. An isolated host cell having the expression vector of claim 1.

9. The host cell of claim 8, wherein the host cell is a human embryonic kidney cell or a Chinese hamster ovary cell.

10. A method of preparing a receptor-binding domain (RBD) sequence of SARS-CoV-2 spike glycoprotein comprising:
    transfecting the expression vector of claim 1 into a host cell;
    filtering the medium through a filter membrane; and
    harvesting the RBD protein comprising binding the RBD protein with an affinity binding bead, washing in a first imidazole-containing buffer to remove impurities, eluting in a second imidazole-containing buffer, and removing an affinity tag of the RBD protein by a tobacco etch virus protease to obtain a tag-free RBD protein.

11. The method of claim 10, wherein the host cell is a human embryonic kidney cell or a Chinese hamster ovary cell.

12. The method of claim 10, wherein the pore size of the filter membrane is approximately 0.22 μm.

13. The method of claim 10, wherein the affinity binding bead is Ni-NTA.

14. The method of claim 10, wherein the imidazole concentration of the first imidazole-containing buffer is approximately from 20 mM to 100 mM; wherein the imidazole concentration of the second imidazole-containing buffer is approximately 200 mM.

* * * * *

SEQUENCE LISTING

<160> NUMBER OF SEQ ID NOS: 3

<210> SEQ ID NO 1
<211> LENGTH: 644
<212> TYPE: DNA
<213> ORGANISM: SARS-coronavirus-2

<400> SEQUENCE: 1

```
agggtgcagc ccaccgagag catcgtgagg ttccccaaca tcaccaacct gtgcccttc      60 ggcgaggtgt tcaacgccac caggttcgcc agcgtgtacg cctggaacag gaagaggatc   120
agcaactgcg tggccgacta cagcgtgctg tacaacagcg ccagcttcag caccttcaag   180
tgctacggcg tgagccccac caagctgaac gacctgtgct tcaccaacgt gtacgccgac   240
agcttcgtga tcagggcga cgaggtgagg cagatcgccc ccggccagac cggcaagatc   300
gccgactaca actacaagct gcccgacgac ttcaccggct gcgtgatcgc ctggaacagc   360
aacaacctgg acagcaaggt gggcggcaac tacaactacc tgtacaggct gttcaggaag   420
agcaacctga agcccttcga gagggacatc agcaccgaga tctaccaggc cggcagcacc   480
ccctgcaacg gcgtggaggg cttcaactgc tacttccccc tgcagagcta cggcttccag   540
cccaccaacg gcgtgggcta ccagccctac agggtggtgg tgctgagctt cgagctgctg   600 cacgccccg ccaccgtgtg cggccccaag aagagcacca acta                      644
```

<210> SEQ ID NO 2
<211> LENGTH: 214
<212> TYPE: PRT
<213> ORGANISM: SARS-coronavirus-2

<400> SEQUENCE: 2

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205
```

Pro Lys Lys Ser Thr Asn
    210

<210> SEQ ID NO 3
<211> LENGTH: 772
<212> TYPE: DNA
<213> ORGANISM: SARS-coronavirus-2

<400> SEQUENCE: 3

| | | | | | |
|---|---|---|---|---|---|
| gaattcgcca | ccatgaagtg | ggtgaccttc | atcagcctgc | tgttcctgtt | cagcagcgcc | 60 |
| tacagccacc | accaccacca | ccacagcagc | ggcggcgaga | acctgtactt | ccagggcagg | 120 |
| gtgcagccca | ccgagagcat | cgtgaggttc | cccaacatca | ccaacctgtg | ccccttcggc | 180 |
| gaggtgttca | acgccaccag | gttcgccagc | gtgtacgcct | ggaacaggaa | gaggatcagc | 240 |
| aactgcgtgg | ccgactacag | cgtgctgtac | aacagcgcca | gcttcagcac | cttcaagtgc | 300 |
| tacggcgtga | gccccaccaa | gctgaacgac | ctgtgcttca | ccaacgtgta | cgccgacagc | 360 |
| ttcgtgatca | gggcgacga | ggtgaggcag | atcgccccg | gccagaccgg | caagatcgcc | 420 |
| gactacaact | acaagctgcc | cgacgacttc | accggctgcg | tgatcgcctg | gaacagcaac | 480 |
| aacctggaca | gcaaggtggg | cggcaactac | aactacctgt | acaggctgtt | caggaagagc | 540 |
| aacctgaagc | ccttcgagag | ggacatcagc | accgagatct | accaggccgg | cagcaccccc | 600 |
| tgcaacggcg | tggagggctt | caactgctac | ttccccctgc | agagctacgg | cttccagccc | 660 |
| accaacggcg | tgggctacca | gccctacagg | gtggtggtgc | tgagcttcga | gctgctgcac | 720 |
| gcccccgcca | ccgtgtgcgg | ccccaagaag | agcaccaact | aatgcagtcg | ac | 772 |